(12) United States Patent
Eliu et al.

(10) Patent No.: US 7,476,260 B2
(45) Date of Patent: Jan. 13, 2009

(54) DISULFIDE DYES, COMPOSITION COMPRISING THEM AND METHOD OF DYEING HAIR

(75) Inventors: Victor Paul Eliu, Lörrach (DE); Beate Fröhling, Steinen (DE); Dominique Kauffmann, Illzach (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 295 days.

(21) Appl. No.: 11/547,571

(22) PCT Filed: Mar. 29, 2005

(86) PCT No.: PCT/EP2005/051412

§ 371 (c)(1),
(2), (4) Date: Oct. 3, 2006

(87) PCT Pub. No.: WO2005/097051

PCT Pub. Date: Oct. 20, 2005

(65) Prior Publication Data

US 2008/0295260 A1 Dec. 4, 2008

(30) Foreign Application Priority Data

Apr. 8, 2004 (EP) .................................. 04101455
Nov. 23, 2004 (EP) .................................. 04105995

(51) Int. Cl.
*A61Q 5/10* (2006.01)
*C09B 31/02* (2006.01)

(52) U.S. Cl. ................ 8/405; 8/406; 8/409; 8/426; 8/432; 8/435; 8/437; 8/565; 8/566; 8/567; 8/568; 8/570; 8/571; 8/575; 132/202; 132/208; 534/759

(58) Field of Classification Search .............. 8/405, 8/409, 426, 432, 435, 437, 565, 566, 567, 8/568, 570, 571, 575; 132/202, 208; 534/759
See application file for complete search history.

(56) References Cited

U.S. PATENT DOCUMENTS

| 3,225,025 | A | * | 12/1965 | Jeremias et al. | 534/745 |
| 4,751,286 | A | | 6/1988 | Packard et al. | 530/388 |
| 6,005,085 | A | | 12/1999 | Ueno et al. | 534/651 |
| 2001/0044975 | A1 | | 11/2001 | Matsunaga et al. | 8/405 |
| 2003/0106168 | A1 | | 6/2003 | Tian et al. | 8/405 |
| 2004/0134382 | A1 | | 7/2004 | Wight et al. | 106/31.47 |

FOREIGN PATENT DOCUMENTS

| EP | 0 913 430 | 5/1999 |
| EP | 1 133 976 | 9/2001 |
| WO | 02/070609 | 9/2002 |
| WO | 03/099242 | 12/2003 |

OTHER PUBLICATIONS

STIC Search Report dated Sep. 5, 2008.*
Asquith et al.; Journal of the Society of dyers and colourists, Bradford, GB, vol. 89, No. 5, (May 1973) pp. 168-172(XP 009016863).
English language abstract of WO 03/099242 printed on Jul. 24, 2007 from esp@cenet web site, (2003).

* cited by examiner

*Primary Examiner*—Eisa B Elhilo
(74) *Attorney, Agent, or Firm*—Mervin G. Wood

(57) ABSTRACT

Formula (I) wherein $R_1$ and $R_2$ each independently from each other are a residue of an organic dye: $Y_1$ and $Y_2$ each independently from each other are unsubstituted or substituted, straightchain or branched, interrupted or uninterrupted —$C_1$-$C_{10}$alkylene-; —$C_5$-$C_{10}$cycloalkylene-; $C_5$-$C_{10}$arylene; or —$C_5$-$C_{10}$arylene-($C_1$-$C_{10}$alkylene)-; $Z_1$ and $Z_2$ independently from each other are Formula (II) are each independently from each other hydrogen; or unsubstituted or substituted, straight-chain or branched, mono-cyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl); r, q and n independently from each other are 0 or 1, if n is 0, $Z_3$ is hydrogen; and if n is 1, $Z_3$ is —S—: with the proviso that the method does not comprise treating the fiber with an enzyme of the type of a protein disulfidisomerase (EC 5.3.4.1). Further, the present invention relates to novel disulfid compounds, compositions thereof, especially comprising other dyes, and to processes for their preparation.

26 Claims, No Drawings

DISULFIDE DYES, COMPOSITION COMPRISING THEM AND METHOD OF DYEING HAIR

FIELD OF THE INVENTION

The present invention relates to novel sulfide dyes, compositions thereof, to processes for their preparation and to their use for the dyeing of organic materials, such as keratin fibers, wool, leather, silk, cellulose or polyamides, especially keratin-containing fibers, cotton or nylon, and preferably hair, more preferably human hair.

BACKGROUND OF THE INVENTION

It is known, for example, from WO 95/01772 that cationic dyes can be used to dye organic material, for example keratin, silk, cellulose or cellulose derivatives, and also synthetic fibers, for example polyamides. Cationic dyes exhibit very brilliant shades. A disadvantage is their unsatisfactory fastness to washing.

R. S. Asquith, P. Carthew and T. T. Francis describe in JSDC from May 1973, pages 168-172 that ortho-azo disulfide dyes do not lead to covalent bonding with keartin fiber of wool, and that para-azo disulfide dyes underwent only at high concentration some covalent bindings with wool.

SUMMARY OF THE INVENTION

The actual technical problem of the present invention was to provide dyes that are distinguished by deep dying having good fastness properties with respect to washing, light, shampooing and rubbing.

DETAILED DESCRIPTION OF THE INVENTION

Accordingly, the present invention relates to a method of dyeing keratin-containing fibers, comprising treating the fiber with at least one sulfide dye of formula

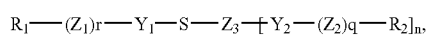
(1)

wherein
$R_1$ and $R_2$ each independently from each other are a residue of an organic dye;
$Y_1$ and $Y_2$ each independently from each other are unsubstituted or substituted, straight-chain or branched, interrupted or uninterrupted —$C_1$-$C_{10}$alkylene; —$C_5$-$C_{10}$cycloalkylene-; $C_5$-$C_1$arylene; or —$C_5$-$C_{10}$arylene-($C_1$-$C_{10}$alkylene);
$Z_1$ and $Z_2$ independently from each other are —C(O)—; —$C_2$-$C_{12}$alkenylene-; —($CH_2CH_2$—O$)_{1-5}$—; $C_1$-$C_{10}$alkylene($C_5$-$C_{10}$arylene)-; —$C_5$-$C_{10}$arylene-; —$C_5$-$C_{10}$cycloalkylene-; —C(O)O—;

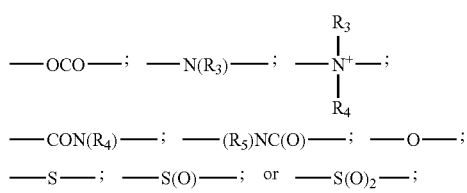

$R_3$, $R_4$ and $R_5$ are each independently from each other hydrogen; or unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);
r, q and n independently from each other are 0 or 1,
if n is 0,
$Z_3$ is hydrogen; and
if n is 1,
$Z_3$ is —S—;
with the proviso that the method does not comprise treating the fiber with an enzyme of the type of a protein disulfidisomerase (EC 5.3.4.1).

Preferably $Y_1$ and $Y_2$ are unsubstituted or substituted straight-chain or branched interrupted or uninterrupted —$C_5$-$C_{10}$cycloalkylene- or —$C_1$-$C_{10}$alkylene.

Further preferred is the method of the present invention, wherein Disulfid-dyes are used, i.e. wherein in formula (1) n is 1.

More preferred is the method of the present invention, wherein $R_1$ and $R_2$ are identical.

Further more preferred is the method of the present invention, wherein
$Z_1$ and $Z_2$ independently from each are other

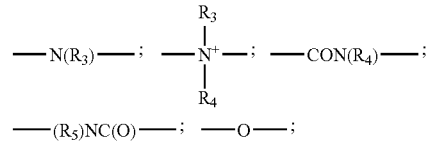

or —S—; and
$R_3$, $R_4$ or $R_5$ are defined as in formula (1)
Further more preferred is the method wherein at least one sulfide dye of formula

(2)

and/or at least one sulfide dye of formula

(3)

is used, wherein
$R_1$, $R_2$, $Z_1$, $Z_2$, $Y_1$, $Y_2$, r and q are defined as in formula (1).

Further more preferred is the method of the present invention, wherein the residue of an organic dye is selected from the group of anionic, cationic, neutral, amphoter and zwitterionic dyes, and especially preferred, wherein the residue of an organic dye is a cationic dye.

Furthermore preferred is the method of the present invention, wherein the residue of an organic dye is selected from the group of anthraquinone, acridine, azo, azomethine, hydrazomethine, benzodifuranone, coumarine, diketopyrrolopyrrol, dioxaxine, diphenylmethane, formazan, indigoid, indophenol, naphthalimide, naphthoquinone, nitroaryl, merocyanine, methin, oxazine, perinone, perylene, pyrenequinone, phtalocyanine, phenazine, quinoneimine, quinacridone, quinophtalone, styryl, triphenylmethane, xanthene, thiazine and thioxanthene dye.

Preferably the residue of an organic dye is selected from azo, azomethine, hydrazomethin, merocyanine, methin and styryl dyes, and more preferred from azo, azomethine dye and hydrazomethine dyes;

Suitable nitroaryl dyes of the present invention are for example selected from the following compounds:

4-amino-1-nitrobenzene, 2-amino-6-chloro-4-nitrophenol, 2-amino-3-nitrophenol, 2-amino-1-nitrobenzene, 1,4-diamino-2-nitrobenzene, 4-acetylamino-1-amino-2-nitrobenzene, 1,2-diamino-4-nitrobenzene, 1-amino-2-methyl-6-nitrobenzene, 3-amino-6-methylamino-2-nitropyridine (Azarot), pikraminacid, 4-amino-3-nitrophenol, 4-amino-2-nitrophenol, 6-nitro-o-toluidine, 1,4-bis-(2-hydroxyethyl)amino-2-nitrobenzene, 1-(2-hydroxyethyl) amino-2-nitro-benzene (HC Yellow No. 2), 1-(2-hydroxyethyl)amino-2-(2-hydroxyethyl) oxy-4-nitro-benzene (HC Yellow No. 4), 1-amino-2-(2-hydroxyethyl) amino-5-nitro-benzene (HC Yellow No. 5), 1-(2, 3-dihydroxypropyl) amino-4-trifluormethyl-2-nitro-benzene (HC Yellow No. 6), 1-(2-hydroxyethyl)amino-4-chloro-2-nitro-benzene (HC Yellow No. 12), 1-amino-2-nitro-4-[bis(2-hydroxyethyl)] amino-benzene (HC Red Mo. 13), 4-chloro-2,5-bis [(2, 3-dihydroxypropyl)amino]-1-nitro-benzene (HC Red No. 11), 1-amino-5-chloro-4-(2, 3-dihydroxypropyl) amino-benzene (HC Red No. 10), 1-amino-2-nitro-4-(2-hydroxyethyl)amino-benzene (HC Red No. 7), 2-chloro-5-nitro-N-(2-hydroxyethyl)-1,4-phenylendiamine, 1-[(2-hydroxyethyl)-amino]-2-nitro-4-amino-benzene (HC Red No. 3), 4-amino-2-nitro-diphenylamine (HC Red No. 1), 2-nitro-4'-hydroxy-diphenylamine (HC Orange No. 1), 1-amino-3-methyl-4-(2-hydroxyethyl)amino-6-nitrobenzene (HC Violet No. 1), 2-(2-hydroxyethyl)amino-5-(bis (2-hydroxyethyl)) amino-1-nitro-benzene (HC Blue No. 2), 1-(2-hydroxyethyl)amino-2-nitro-4-N-ethyl-N-(2-hydroxyethyl) amino)-benzene (HC Blue No. 12), 4-amino-3,5-dinitro-benzoic acid, 4-amino-2-nitrodiphenylamin-2'-carbonic acid, 2-(4'-amino-2'-nitroanilino)-benzoic acid, 6-nitro-2,5-diaminopyridine, 2-amino-6-chloro-4-nitrophenol, 4-amino-4'-nitrostilben-2,2'-disulfonic acid, 4'-amino-4-nitrodiphenylamin-2-sulfonic acid, 4'-amino-3'-nitrobenzophenon-2-carbonic acid, 1-amino-4-nitro-2-(2'-nitrobenzylidenamino)-benzene, 2-[2-(diethylamino) ethylaminol-nitroaniline, 3-amino-4-hydroxy-5-nitrobenzolsulfonic acid, 3-amino-3'-nitrobiphenyl, 3-amino-4-nitro-acenaphthen, 2-amino-1-nitronaphthaline, 5-amino-6-nitrobenzo-1,3-dioxol, 2-amino-6-nitrobenzothiazol, 4-(3-hydroxypropyl)amino-3-nitro-phenol (HC Red BN), 2-amino-4,6-dinitro-phenol, 3-nitro-4-(2-hydroxyethyl)-aminophenol, 2-(2-hydroxyethyl)amino-4,6-dinitrophenol, 2-amino-6-chlor-4-nitrophenol, 2-chloro-6-ethylamino-4-nitro-phenol, 1-(2-hydroxyethyl)amino-4-methyl-2-nitrobenzene, 1-(2'-ureidoethyl)amino-4-nitrobenzene, 4-amino-2-nitro-diphenylamin-2'-carbonic acid, 6-nitro-1,2,3,4-tetrahydrochinoxaline and 4-ethylamino-3-nitrobenzoic acid.

Suitable anthraquinone dyes suitable for the method of the present invention are the following compounds:1-[(3-aminopropyl)amino]-anthraquinone (HC Red No. 7), 2-[(2-aminoethyl)amino]-anthraquinone (HC Orange No. 5), 1,4,5,8-tetramino-anthrachinone (Disperse Blue 1), 1-[(2-Hydroxyethyl)amino]-4-methylamino-anthraquinone (Disperse Blue 3), 1,4-[(2-hydroxyethyl)amino]-5,8-dihydroxy-anthraquinone (Disperse Blue 7), 1,4-diamino-2-methoxy-anthraquinone (Disperse Red 11), 1-amino-4-hydroxy-anthraquinone (Disperse Red 15), 1,4-diamino-anthraquinone (Disperse Violet 1), 1-amino-4-methylamino-anthrachinone (Disperse Violet 4) and 1-amino-4-isopropylamino-anthraquinone (Disperse Violet 15).

Suitable azo dyes are for example the following compounds:

4-amino-4'-[bis(2-hydroxyethyl)] amino-azobenzene (Disperse Black 9), 4-amino-4'-nitro-azobenzene (Disperse Orange 3), 3-hydroxy-4-[(2-hydroxy-naphth-1-yl) azo)-7-nitro-naphthalin-1-sulfonic acid-chromcomplex (Acid Black 52), 1-amino-2-(3'-nitro-phenylazo)-7-phenylazo-8-naphthol-3,6-disulfonic acid (Acid blue Nr. 29), 1-amino-2-(2'-hydroxy-4'-nitrophenylazo)-8-naphthol-3,6-disulfonic acid (Palatinchrome green), 1-amino-2-(3'-chlor-2'-hydroxy-5'-nitrophenylazo)-8-naphthol-3,6-disulfonic acid (Gallion) and diamino-3',5'-dinitro-2'-hydroxy-5-methyl-azobenzene (Mordant brown 4).

Suitable cationic dyes are the following compounds: N-[4-[[4-(diethylamino) phenyl][4-(ethylaminoynaphth-1-yl]methylen]-2,5-cyclohexadien-1-yliden]-N-ethyl-ethaniminium-chloride (Basic Blue No. 7), N-{4-[(4-(dimethylamino) phenyl) 4-(phenylamino)-1-naph-thalenyl] methylen}-2,5-cyclohexadion-1-ylidene]-N-methyl-methaniminiumchloride (Basic Blue 26), 4-[(4-aminophenyl) (4-imino-2,5-cyclohexadien-1-yliden) methyl]-2-methyl-anilin-hydrochloride (Basic Violet 14), N-{3-[[4,5-dihydro-3-methyl-5-oxo-1-phenyl-1H-pyrazol-4-yl) azo] phenyl}-N,N,N-trimethylammoniumchloride (Basic Yellow 57), N-[7-hydroxy-8-[(2-methoxyphenyl) azo]-naphth-2-y]-N,N,N-trimethylammonium-chloride (Basic Red 76), N-[4-[[4-(dimethylamino) phenyl][4-(phenylamino)-naphth-1-yl]-methylene]-2,5-cyclohexadien-1-yliden]-N-methyl-2-methaniminiumchloride (Basic Blue 99), 18-[(4'-amino-2'-nitro)phenyl) azo]-7-hydroxy-naphth-2-yl]-trimethylammoniumchloride (Basic Brown 16), [8-((4'-amino-3'-nitrophenyl) azo)-7-hydroxy-naphth-2-yl]-trimethylammoniumchloride (BasicBrown 17), Basic Yellow 87, Basic Red 51 or Basic Orange 31.

Most preference is given to a method wherein the fiber is treated with at least one sulfide dye selected from the dyes of formula

(7)

and

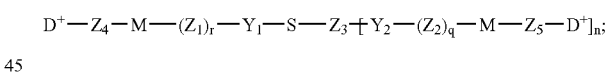

(8)

wherein $Z_4$ and $Z_5$ independently from each other are a bivalent radical selected from $-N=N-$; $-CR_6=N-$; $-N=CR_7-$; $-NR-N=CR_9-$; and $-R_{10}C=N-NR_{11}-$; wherein $R_6$, $R_7$, $R_8$, $R_9$, $R_{10}$ and $R_{11}$ independently from each other are hydrogen; unsubstituted or substituted $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl; and $D^+$ is a cationic radical of a substituted or unsubstituted aromatic or heterocyclic compound, wherein the cationic charge may be part of the aromatic compounds or part of the substituent;

M is a bivalent radical of an aromatic or heteroaromatic substituted or unsubstituted compound;

T is a radical of an aromatic substituted or unsubstituted compound;

Q⁺ is a cationic biradical of a substituted or unsubstituted aromatic or heteroaromatic compound; and $Z_1, Z_2, Z_3, Y_1, Y_2$, n, r and q are defined as in formula (1).

Especially preferred is a method, wherein D is a radical of a cationic aromatic substituted or unsubstituted heterocyclic compound of formulae

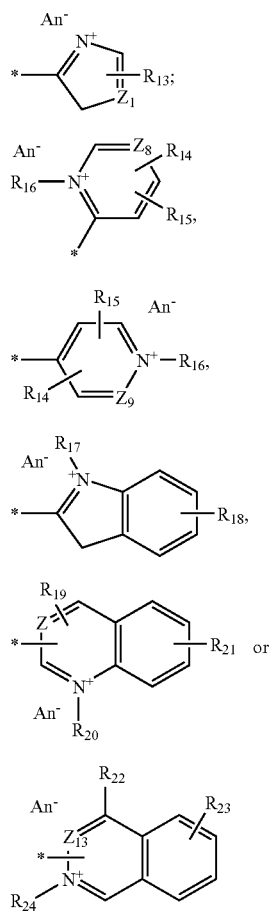

wherein the asterix * indicates the bond to $Z_4$ and/or $Z_5$ of formula (7); and Q⁺ is a cationic bivalent radical of an aromatic heterocyclic compound of formulae

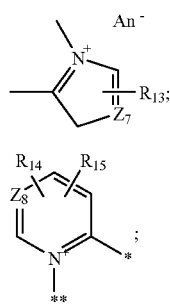

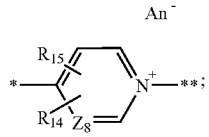

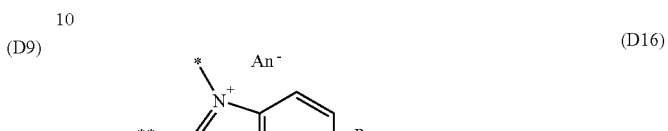

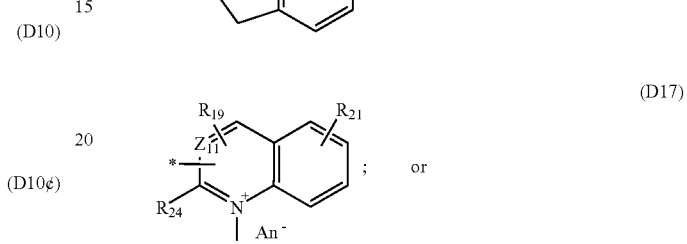

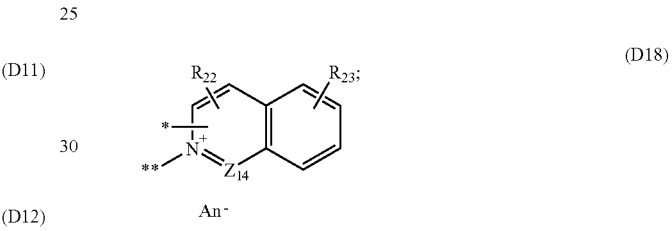

wherein the asterix * indicates a bond to $Z_4$ and/or $Z_5$ of formula (8);

the asterix ** is a bond to $Z_1$ and/or $Z_2$ of formula (8); and

M is a bivalent radical of formulae

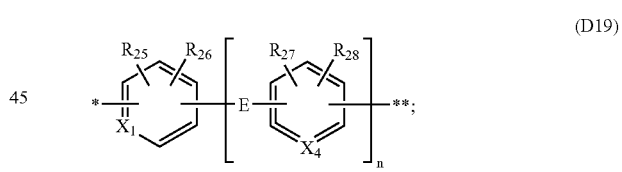

or

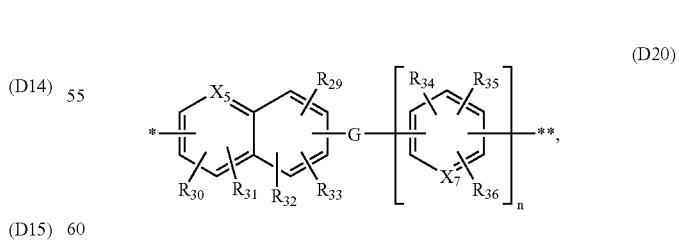

wherein the asterix * indicates the bond to $Z_4$ or/and $Z_5$ of formula (7);

the asterix ** indicates the bond to $Z_1$ and/or $Z_2$ of formula (7); and

T is a radical of the compounds of formulae

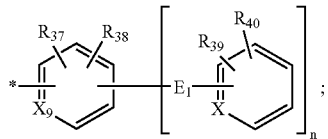 (D21)

or

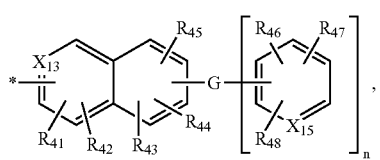 (D22)

The heteroaromatic cycles of the radicals of the formulae (D9)-(D22) may be interrupted by one or more than one —O—, —S—, —(SO$_2$)—, —C$_1$-C$_{10}$alkylene or —(NR$_{52}$)—;

Very specially preferred is a method, wherein D$^+$ is a radical of a cationic aromatic substituted or unsubstituted heterocyclic compound of formulae

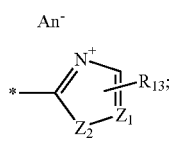 ((9)

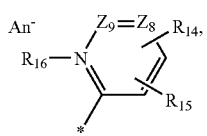 (10)

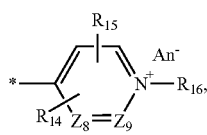 (10')

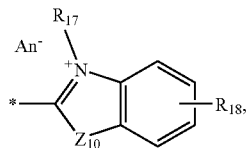 (11)

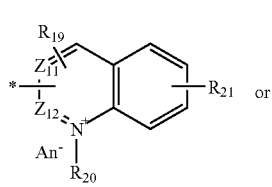 (12)

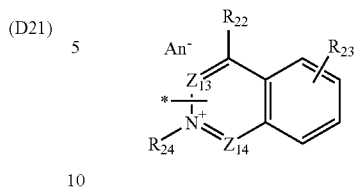 (13)

wherein the asterix * indicates the bond to Z$_4$ and/or Z$_4$ of formula (7); and Q$^+$ is a cationic bivalent radical of an aromatic heterocyclic compound of formulae

 (14)

 (15)

 (15¢)

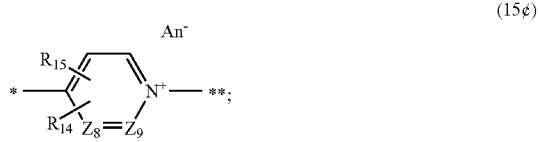 (16)

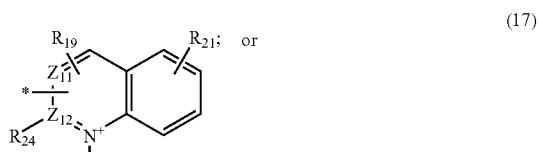 (17)

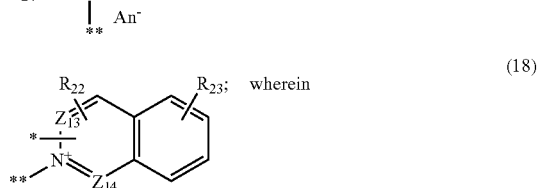 (18)

the asterix * indicates a bond to Z$_4$ and/or Z$_4$ of formula (8); the asterix ** is a bond to Z$_1$ and/or Z$_2$ of formula (8); and M is a bivalent radical of formulae

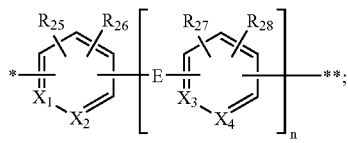
(19)

or

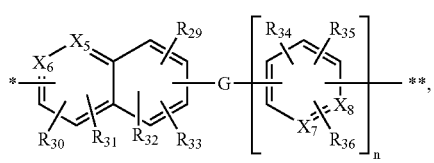
(20)

wherein
the asterix * indicates the bond to $Z_4$ or/and $Z_5$ of formula (7);
the asterix ** indicates the bond to $Z_1$ and/or $Z_2$ of formula (7); and
T is a radical of the compounds of formulae

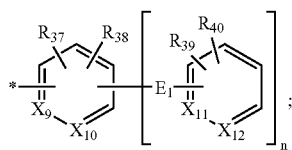
(21)

or

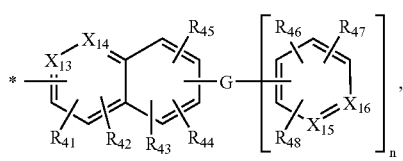
(22)

wherein
the asterix * indicates the bond to $Z_4$ and/or $Z_5$ of compound of formula (8).

In the formulae (D9)-(D22) and (9)-(22)
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$ and $X_{16}$ are independently from each other N or a radical of $CR_{49}$, $Z_6$ is —O—; —S—; or a radical of $NR_{50}$,
$Z_7$, $Z_8$, $Z_9$, $Z_{10}$, $Z_{11}$, $Z_{12}$, $Z_{13}$ and $Z_{14}$ are independently from each other N or a radical of $CR_{51}$;
E, $E_1$, G and $G_1$ are independently from each other —O—, —S—, —($SO_2$)—, —$C_1$-$C_{10}$alkylene or —($NR_{52}$)—;
$R_{13}$, $R_{14}$, $R_{15}$, $R_{18}$, $R_{19}$, $R_{21}$, $R_{22}$, $R_{23}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, $R_{48}$, $R_{49}$ and $R_{51}$ are independently from each other hydrogen; halogen; $C_1$-$C_{14}$alkyl, which is saturated or unsaturated, linear or branched, substituted or unsubstituted, or interrupted or uninterrupted with heteroatoms; a radical of phenyl, which substituted or unsubstituted; a of carboxylic acid radical; sulfonic acid radical; hydroxy; nitrile; $C_1$-$C_{16}$alkoxy, (poly)-hydroxy-$C_2$-$C_4$-alkoxy; halogen; sulfonylamino; $SR_{60}$, $NHR_{53}$; $NR_{54}R_{55}$; $OR_{61}$; $SO_2$; $COOR_{62}$; $NR_{56}COR_{58}$; or $CONR_{57}$; and $R_{12}$, $R_{16}$, $R_{17}$, $R_{20}$, $R_{24}$, $R_{50}$, $R_{52}$, $R_{53}$, $R_{54}$, $R_{55}$, $R_{56}$, $R_{57}$, $R_{58}$, $R_{60}$, $R_{61}$ and $R_{62}$ are each independently of the other hydrogen; unsubstituted or substituted $C_1$-$C_{14}$alkyl, $C_2$-$C_{14}$alkenyl, $C_5$-$C_{10}$aryl, $C_6$-$C_{10}$aryl-($C_1$-$C_{10}$alkyl), or —$C_1$-$C_{10}$alkyl($C_5$-$C_{10}$aryl); and An is an anion.

Very especially most preferred is a method, wherein $D^+$ is a radical of a cationic aromatic substituted or unsubstituted heterocyclic compound of formulae (23)

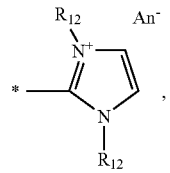

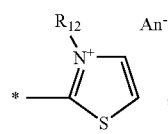
(28)

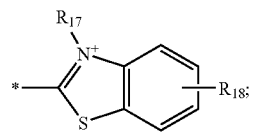
(29)

(30)

(27)

wherein
* is a bond to $Z_4$ and/or $Z_5$ of formula (7); and
$Q^+$ is a biradical of a cationic aromatic substituted or unsubstituted heterocyclic compound of formulae

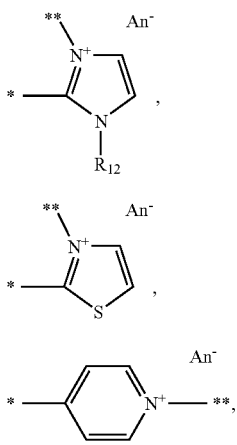

(28) wherein
 * is a bond to $Z_4$ and/or $Z_5$ of formula (8);
 ** is a bond to and $Z_1$ and/or $Z_2$ of formula (8); and
 M is a bivalent radical of formula

(33)

(29) wherein
 * is a bond to $Z_4$ and/or $Z_5$ of formula (7) or (8),
 ** is a bond to and $Z_1$ and/or $Z_2$ of formula (7) or (8); and
 n is 1 or 0;
 and
 T is a radical of formulae (30)

(31)

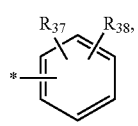
(34)

(32) wherein
 $R_{12}$, $R_{16}$, $R_{17}$, $R_{18}$, $R_{25}$, $R_{26}$, $R_{37}$, $R_{38}$ and An are defined as in claim 14.

Furthermore, very especially most preferred is a method, comprising disulfide dyes of formulae

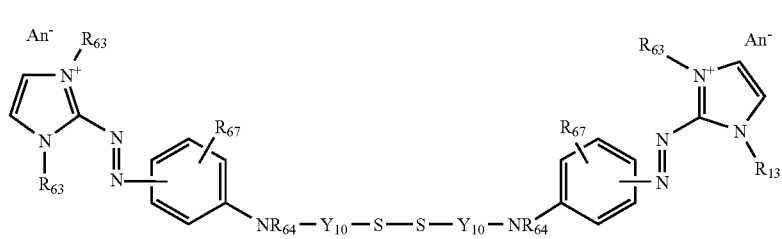
(35)

wherein
$R_{63}$ is hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl-($C_1$-$C_{10}$alkyl); $C_1$-$C_{10}$ alkyl-($C_5$-$C_{10}$aryl); $C_6$-$C_{10}$aryl; and
$R_{64}$ is hydrogen; unsubstituted or substituted, straight-chain or branched, interrupted or uninterrupted $C_1$-$C_{14}$alkyl, $C_5$-$C_{10}$cycloalkyl, $C_5$-$C_{10}$aryl, or $C_5$-$C_{10}$aryl-($C_1$-$C_{10}$alkyl); $C_1$-$C_{10}$alkyl ($C_1$-$C_{10}$aryl)
$R_{67}$ is hydrogen; or a radical of formula,

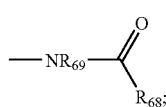
(35a)

$Y_{10}$ is unsubstituted or substituted, straight-chain or branched, monocyclic, from $C_3$-alkyl upwards, or polycyclic, from $C_5$-alkyl upwards, interrupted or uninterrupted, $C_1$-$C_{10}$alkylene; $C_5$-$C_{10}$arylene-($C_1$-$C_{10}$alkylene); $C_1$-$C_{10}$alkylene-($C_5$-$C_{10}$arylene); or —$C_5$-$C_{10}$arylene; and $R_{68}$ and $R_{69}$ are each independently of the other hydrogen, unsubstituted or substituted $C_1$-$C_{14}$alkyl, $C_2$-$C_{14}$alkenyl, —$C_5$-$C_{10}$arylen-($C_1$-$C_{10}$alkyl), —$C_1$-$C_{10}$alkylen-($C_5$-$C_{10}$aryl), $C_5$-$C_{10}$aryl,

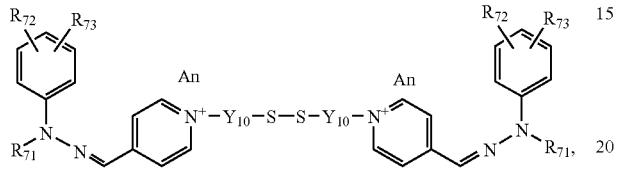

(36)

wherein $R_{71}$ is hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl; $C_1$-$C_{10}$alkyl-($C_5$-$C_{10}$aryl); $C_5$-$C_{10}$aryl-($C_1$-$C_{10}$alkyl);

$R_{72}$ and $R_{73}$ are each independently of the other hydrogen; $C_1$-$C_{14}$alkyl; $C_2$-$C_{14}$alkenyl; a radical of acarboxylic; a radical of a sulfonic acid; $C_5$-$C_{10}$aryl: hydroxy, nitril, $C_1$-$C_{16}$alkoxy, (poly)-hydroxy-$C_2$-$C_4$-alkoxy, carboxylic acid; halogen; sulfonylamino; $SR_{60}$; $NHR_{53}$; $NR_{54}R_{55}$; $OR_{61}$; $COOR_{62}$; $NR_6COR_{58}$; or $CONR_{57}$;

$R_{53}$, $R_{54}$, $R_{55}$, $R_{56}$, $R_{57}$, $R_{58}$, $R_{60}$, $R_{61}$ and $R_{62}$ are each independently of the other hydrogen; unsubstituted or substituted $C_1$-$C_{14}$alkyl; $C_2$-$C_{14}$alkenyl; —$C_5$-$C_{10}$arylen-($C_1$-$C_{10}$alkyl); —$C_1$-$C_{10}$alkylene($C_5$-$C_{10}$aryl); or $C_5$-$C_{10}$aryl;

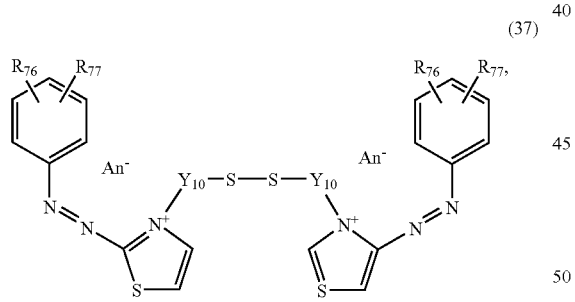

(37)

wherein $R_{76}$ and $R_{77}$ are each independently of the other hydrogen, $C_1$-$C_{14}$alkyl, which is saturated or unsaturated, linear or branched, substituted or unsubstituted, or interrupted or uninterrupted with heteroatoms; a radical of phenyl, which substituted or unsubstituted; a radical of carboxylic acid; $C_5$-$C_{10}$aryl: a radical of hydroxy, nitril, $C_1$-$C_{15}$alkoxy, (poly)-hydroxy-$C_2$-$C_4$-alkoxy, carboxylic acid, sulfonic acid; halogen, sulfonylamino, $SR_{60}$, $NHR_{53}$ or $NR_{54}R_{55}$, $OR_{61}$, $SO_2$, $COOR_{62}$, $NR_{56}COR_{58}$, $CONR_{57}$;

$R_{53}$, $R_{54}$, $R_{55}$, $R_{56}$, $R_{57}$, $R_{58}$, $R_{60}$, $R_{61}$, and $R_{62}$ are each independently of the other hydrogen, unsubstituted or substituted $C_1$-$C_{14}$alkyl, $C_1$-$C_{14}$alkenyl, —$C_5$-$C_{10}$arylen-($C_1$-$C_{10}$alkyl), —$C_1$-$C_{10}$alkylen($C_5$-$C_{10}$aryl), $C_5$-$C_{10}$aryl,

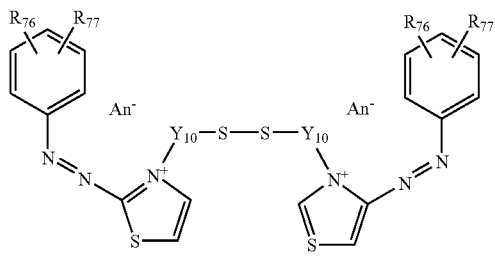

(38)

wherein $R_{79}$, $R_{78}$ and $R_{80}$ are each independently of the other hydrogen; $C_1$-$C_{14}$alkyl, which is saturated or unsaturated, linear or branched, substituted or unsubstituted, or interrupted or uninterrupted with heteroatoms; a radical of phenyl, which substituted or unsubstituted; a radical of carboxylic acid; $C_5$-$C_{10}$aryl; a radical of hydroxy, nitril, $C_1$-$C_{16}$alkoxy, (poly)-hydroxy-$C_2$-$C_4$-alkoxy; carboxylic acid; sulfonic acid; halogen; sulfonylamino; $SR_{60}$; $NHR_{53}$; $NR_{54}$, $R_{55}$; $OR_{61}$; $SO_2$; $COOR_{62}$; $NR_{56}COR_{58}$; or $CONR_{57}$;

$R_{53}$, $R_{54}$, $R_{55}$, $R_{56}$, $R_{57}$, $R_{58}$, $R_{60}$, $R_{61}$, and $R_{62}$ are each independently of the other hydrogen; unsubstituted or substituted $C_1$-$C_{14}$alkyl; $C_2$-$C_{14}$alkenyl; $C_5$-$C_{10}$arylene-($C_1$-$C_{10}$alkyl), $C_1$-$C_{10}$alkylene($C_5$-$C_1$aryl), $C_5$-$C_{10}$aryl;

More preferred are:

compounds of formula (35), wherein $R_{63}$ is methyl;
compounds of formula (36), wherein $R_{72}$ is hydrogen; and $R_{72}$ is in the para-postion of the phenyl moiety;
compounds of formula (37), wherein $R_{76}$ is hydrogen; and $R_{77}$ is in the para-postion of the phenyl moiety;
compounds of formula (38), wherein $R_{78}$ is hydrogen; and $R_{79}$ is in the para-postion of the phenyl moiety.

The compounds of formula

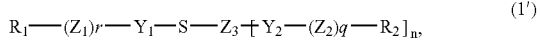

(1')

wherein $R_1$ and $R_2$ each independently from each other are a residue of an organic dye;

$Y_1$ and $Y_2$ independently from each other are $C_1$-$C_{10}$alkylene;

$Z_1$ and $Z_2$ independently from each other are —C(O)—; —$C_2$-$C_{12}$alkenylene-; —(CH$_2$CH$_2$—O)$_{1-5}$—; $C_1$-$C_{10}$alkylene($C_5$-$C_1$arylene); $C_5$-$C_{10}$arylene; $C_5$-$C_{10}$cycloalkylene, —C(O)O—, —OCO—;

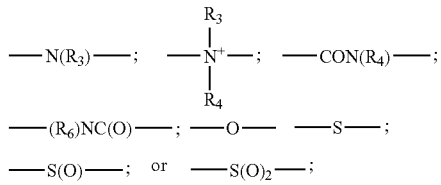

$R_3$, $R_4$ and % are each independently from each other hydrogen; $C_1$-$C_{14}$alkyl; $C_2$-$C_{14}$alkenyl; $C_6$-$C_{10}$aryl; $C_1$-$C_6$alkyl-$C_6$-$C_{10}$aryl; or —$C_5$-$C_{10}C_5$-$C_{10}$aryl;

r, q and n independently from each other are 0; or 1, if n is 0,
$Z_3$ is hydrogen; and
if n is 1,
$Z_3$ is —S—;
are novel and represent another subject of the present invention.

The present invention also relates to the novel compounds of formulae (35), (36), (37) and (38).

Alkylene is generally $C_1$-$C_{10}$alkylene, for example methylene, ethylene, propylene, isopropylene, n-butylene, sec-butylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene or decylene.

Alkylene may be straight-chain, branched, or, from $C_5$alkyl upwards, monocyclic or polycydic, and may be interrupted by hetero atoms, such as such as O, S, —CO—, N, NH, $NR_{54}$—OCO—, —CO(OR$_4$)—, —CONR$_4$—, —(R$_5$)NC(O)—; for example $C_1$-$C_{10}$alkylene may be a reissue such as: —CH$_2$CH$_2$—O—CH$_2$CH$_2$—O—CH$_2$CH$_2$—, or —CH$_2$CH$_2$—O—CH$_2$CH$_2$, —CH$_2$CH$_2$—O—CH$_2$—, —CH$_2$—O—CH$_2$—, —CH$_2$CH$_2$—CH$_2$CH$_2$—C—CH$_2$—CH$_2$—, —CH$_2$CH$_2$—CH(N(CH$_3$)$_2$)—CH$_2$—CH$_2$—, CH$_2$—NH$_2$—CH$_2$—CH$_2$, or —CH$_2$CH$_2$—NH—CH$_2$CH$_2$—, —CH$_2$CH$_2$—NCH$_3$—CH$_2$CH$_2$—, or —CO—CH$_2$—, or —CH$_2$CO—, or —CH$_2$CH$_2$—NHCO—CH$_2$CH$_2$, or —CH$_2$CH$_2$—CONH—CH$_3$—CH$_2$CH$_2$—, —CH$_2$CH$_2$—NCH$_3$CO—CH$_2$CH$_2$—, or —CH$_2$CH$_2$—CONCH$_3$—CH$_3$—CH$_2$CH$_2$—, or —CH$_2$—NHCO—CH$_2$CH$_2$—, or —CH$_2$CH$_2$—NHCO—CH$_2$—, or —CH$_2$CH$_2$—CONH—CH$_2$— or —CH$_2$—CONH—CH$_2$CH$_2$—.

Arylene is generally $C_6$-$C_{10}$arylene; for example phenyl or naphthyl;

Aryl-alkylene is for example $C_5$-$C_{10}$aryl-$C_1$-$C_{10}$alkylene, $C_6$-$C_{10}$aryl-$C_1$-$C_2$alkylene, alkyl-arylene is for example $C_1$-$C_{10}$alkyl-$C_5$-$C_{10}$arylene or $C_1$-$C_2$alkyl-$C_6$-$C_{10}$arylene.

$C_5$-$C_{10}$cycloalkylene is for example cyclopentylene, cyclohexylene, morpholylene or piperidinylene.

In the present invention substituents may be chosen from the following groups:
hydroxyl, $C_1$-$C_{16}$alkyl, $C_5$-$C_{10}$aryl, $C_1$-$C_{16}$alkoxy, —COOH, sulfonic acid, sulfonylamino, —SR$_{50}$, —OCO—, —COOR$_4$, —CONR$_4$, —(R$_5$)NC(O), —S(O)—, —SO$_2$, cyanide, nitrile, halide, aryl, aralkyl, alkylaryl and NR$_{54}$R$_{55}$, wherein $R_4$, $R_5$, $R_{54}$, $R_{55}$ and $R_{60}$ have the same definition and preferences as given above.

$C_1$-$C_{16}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl, tetradecyl, pentadecyl or haxadecly.

$C_1$-$C_6$alkoxy is O—$C_1$-$C_6$alkyl, preferably O—C—$C_4$alkyl.

$C_5$-$C_{10}$aryl-$C_1$-$C_{10}$alkylene is, for example, phenyl-$C_1$-$C_{10}$alkylene or naphthyl-$C_1$-$C_{10}$alkylene.

$C_6$-$C_{10}$aryl-$C_1$-$C_2$alkylene and $C_1$-$C_2$alkyl-$C_6$-$C_{10}$arylene are, for example, phenyl-$C_1$-$C_{10}$alkylene or naphthyl-$C_1$-$C_{10}$alkylen.

Halide is, for example, fluoride, chloride, bromide or iodide, especially chloride and fluoride.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

The anion is especially a halide, preferably chloride or fluoride, sulfate, hydrogen sulfate, methyl sulfate, ethyl sulfate, phosphate, formate, acetate or lactate.

The anion is more especially fluoride, chloride, methyl sulfate, ethyl sulfate, formate or acetate.

In the present invention protein disulfidisomerase (EC 5.3.4.1) is an enzyme of the enzyme category EC 5.3.4.1. These enzymes preferably catalyse the isomerisation of intermolecular and intramolecular disulfid-bonds in proteins. The EC (Enzyme commission) number is pro-vided from the "Nomenclature Committee of the International Union of Biochemistry and Molecular Biology" (IUBMB). A complete list of the charactertized enzymes of the enzymes categories according to IUBMB is provided by data base of SwissProt under http://1www.expasy.ch.

In the present invention the residue of an organic dye is substituted or unsubstituted.

In the present invention biradical or radical of a heterocyclic compound is for example a biradical or radical of thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl.

Preferred biradical or radical of a heterocyclic compound is for example 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl. More preferred cationic heterocyclic compounds are imidazolyl, pyridinyl, 1,3,4-triazolyl and 1,3-thiazolyl.

In the present invention a biradical or radical of an aromatic compound is for example phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether or azobenzenyl.

The biradical or radical of a heterocyclic or aromatic compound is unsubstituted or mono- or poly-substituted, for example by $C_1$-$C_4$alkyl, $C_1$-$C_4$alkoxy, $C_1$-$C_4$alkylthio, halogen, e.g. fluorine, bromine or chlorine, nitro, trifluoromethyl, CN, SCN, $C_1$-$C_4$alkylsulfonyl, phenylsulfonyl, benzylsulfonyl, di-$C_1$-$C_4$alkylaminosulfonyl, $C_1$-$C_4$alkyl-carbonylamino, $C_1$-$C_4$alkoxysulfonyl or by di-(hydroxy-$C_1$-$C_4$alkyl)-aminosulfonyl.

A further embodiment of the present invention relates to processes for the preparation of the dyes of formula (1).

Generally, the process-comprises a nucleophilic substitution of an organic compound by a sulfide and/or disulfide derivative containing at least one nucleophile group, or a electrophilic substitution of an organic compound by a sulfide and/or disulfid derivative containing at least one electrophilic groups.

A preferred process for the preparation comprises reacting a compound of formula (1a) with the compound of formula (1b) according to the following reaction scheme:

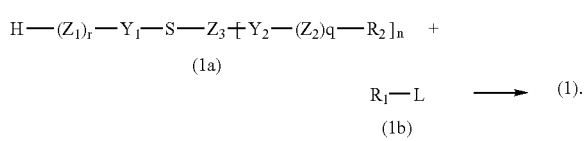

A further preferred process for the preparation of compounds of formula (1) comprises reacting a compound of formula (1c) with the compound of formula (1d) according to the following reaction scheme:

$$L_1-(Z_1)_r-Y_1-S-Z_3+Y_2-(Z_2)_q-R_2]_n +$$
(1c)

$$R_1-H \longrightarrow (1).$$
(1d)

In the formula (1a), (1b), (1c) and (1d)

$L_1$ is a leaving group; and $R_1$, $R_2$, $Z_1$, $Z_2$, $Z_3$, $Y_1$, $Y_2$, r, q and n are defined as in formula (1).

The reaction is generally initiated by contacting; for example by mixing together the starting compounds or by dropwise addition of one starting compound to the other.

Customary, the temperature is in the range of 273 to 300 K, preferably is in the range of 290 to 300 K during the mixing of the starting compounds.

The reaction time is generally dependent on the reactivity of the starting compounds, on the reaction temperature chosen and on the desired conversion. The chosen duration of reaction is usually in the range from one hour to three days.

The reaction temperature for the reaction of the compounds is advisable to select in the range from 273 to 340K, especially in the range from 273 to 335K.

The reaction pressure chosen is generally in the range from 70 kPa to 10 MPa, especially from 90 kPa to 5 MPa, and is more especially atmospheric pressure.

It may by desirable to conduct the reaction of compounds in the presence of a catalyst.

The molar ratio of compound of formula (1a) to the catalyst is generally selected in the range from 10:1 to 1:5, especially in the range from 10:1 to 1:1.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or tertiary amines, for example, such as chinuclidine, N-methylpiperidine, pyridine, trimethylamine, triethylamine, trioctylamine, 1,4-diazabicyclo[2.2.2]octan, chinuclidine, N-methylpiperidine; or alkalimetal acetate, for example such as sodium acetate, potassium acetate, or lithium acetate.

Preferred are potassium acetate, sodium methoxide, pyridine and 1,4-diazabicyclo[2.2.2]-octan.

In addition, the reaction may be carried out with or without a solvent, but is preferably carried out in the presence of a solvent, preferably organic solvents or solvent mixtures.

Solvents are organic solvents and water, or a mixture of organic solvents or a mixture of organic solvents and water.

Organic solvents are for example, protic or aprotic polar organic solvents, such as alcohols, for example methanol, ethanol, n-propanol, isopropanol, butanol or glycols, especially isopropanol, or nitrile, such as acetonitrile or propionitrile, or amide, such as dimethylformamide, di-methylacetamide or N-methylpyridine, N-methylpyrolidone, or sulfoxide, such as dimethylsulfoxide, or mixtures thereof.

The product prepared according to the process of the present invention may be advantageously worked up and isolated, and if desired be purified.

Customary, the work up starts by decreasing the temperature of the reaction mixture in the range from 280 to 300 K, especially in the range from 290 to 300 K.

It may be of advantageous to decrease the temperature slowly, over a period of several hours.

In general, the reaction product is usually filtered and then washed with water or a salt solution and subsequently dried.

Filtration is normally carried out in standard filtering equipment, for example Büchner funnels, filter presses, pressurised suction filters, preferably in vacuo.

The temperature for the drying is dependent on the pressure applied. Drying is usually carried out in vacuo at 50-200 mbar.

The drying is usually carried out at a temperature in the range from 313 to 363 K, especially from 323 to 353 K, and more especially in the range from 328 to 348 K.

Advantageously the product is purified by recrystallisation after isolation.

Organic solvents and solvent mixtures are suitable for the recrystallisation, preferably alcohols, for example methanol, ethanol, 2-propanol or butanol, especially 2-propanol.

The present invention also relates to a process for the preparation of compounds of formula (70)

$$O_2N-\underset{NH_2}{\underset{|}{\overset{F}{\bigcirc}}} \xrightarrow{X-CO-R_{68}} O_2N-\underset{\underset{R_{68}}{\overset{O}{\underset{\|}{\bigcirc}}NH_2}}{\overset{F}{\bigcirc}}, \text{ which comprises}$$

a. acylating of 4-fluoro-3-nitroaniline with an acylating agent as shown in the above formula
b. then reducing the nitro group to the amino group,
c. then diazotizing the acylated 4-Fluoro-3-amino-aniline, and
d. then coupling the diazotized with imidazole, and
e. then alkylating the intermediate compound with an alkylating agent; or
$a_1$) diazotizing and coupling of a compound of formula, and then
$b_1$) alkylating the intermediate compound with an alkylating agent $$H_2N-\underset{}{\bigcirc}-F;$$

wherein $R_{68}$ is hydrogen, unsubstituted or substituted $C_1$-$C_{14}$alkyl, $C_2$-$C_{14}$alkenyl, —$C_5$-$C_{10}$arylen-($C_1$-$C_{10}$alkyl), —$C_1$-$C_{10}$alkylen($C_5$-$C_{10}$aryl), $C_5$-$C_{10}$aryl, The acylation, reduction, diazotation, coupling and alkylation can be conducted by methods known per se.

The dyes of formula (1) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The stability, in particular the storage stability of the dyes according to the invention are excellent.

The multiplicity of shades of the dyes can be increased by combination with other dyes.

Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesver-band der deutschen Industrie-und Handelsunternehmen für Arzneimittel, Reformwaren und Körperpflegemittel e.V., Mannheim.

Furthermore, cationic nitroaniline and anthraquinone dyes are useful for a combination with a dye of formula (1).

The dyes of formula (1) may also be combined with acid dyes, for example the dyes which are known from the international names (Color index), or trade names.

These acid dyes may be used either as single component or in any combination thereof.

The dyes of formula (1) may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes of formula (1) may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, I. 6 to col 3, I. 11;
"Dermatology", edited by Ch. Culnan, H. Maibach, Verag Marcel Dekker Inc., New York, Basle, 1986, Vol. 7, Ch. Zviak, The Science of Hair Care, chapter 8, on p. 264-267 (oxidation dyes).

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives or 2,4,5,6-tetraminopyrimidine derivatives.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, I. 8-29.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, I. 33 to p. 3, I. 11.

Furthermore, autooxidizable compounds may be used in combination with the dyes of formula (1).

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indol, or indol, especially 5,6-dihydroxyindole or 5,6-dihydroxyindole.

The dyes of formula (1) may also be used in combination with naturally occurring dyes, such ashenna red, henna neutral, henna black, camomile blossom, sandalwood, black tea, Rhamnus frangula bark, sage, campeche wood, madder root, catechu, sedre and alkanet root.

Furthermore, the dyes of formula (1) may also be used in combination with capped diazotized compounds.

Suitable diazotized compounds are for example the compounds of formulae (1)-(4) in WO 2004/019897 (bridging gages 1 and 2) and the corresponding watersoluble coupling components (I)-(IV) as disclosed in the same reference on p. 3 to Further preferred dyes or dye combinations which are useful for the combination with a dye of formula (1) according to the present invention are described in (DC-01): WO 95/01772, wherein mixtures of at least two cationic dyes are disclosed, especially p. 2, I. 7 to p. 4, I. 1, preferably p. 4, I. 35 to p. 8, I. 21; formulations p. 11, last §-p. 28, I. 19;

(DC-02): U.S. Pat. No. 6,843,256, wherein cationic dyes are disclosed, especially the compounds of formulae (1), (2), (3) and (4) (col. 1, I. 27-col. 3, I. 20, and preferably the compounds as prepared in the examples 1 to 4 (col. 10, I. 42 to col. 13, I. 37; formulations col. 13, I. 38 to col. 15, I. 8;

(DC-03): EP 970 685, wherein direct dyes are described, especially p. 2, I. 44 to p. 9, I. 56 and preferably p. 9, I. 58 to p. 48, I. 12; processes for dyeing of keratin-containing fibers especially p. 50, I. 15 to 43; formulations p. 50, I. 46 to p. 51, I. 40;

(DC-04): DE-A-19 713 698, wherein direct dyes are described, especially p. 2, I. 61 to p. 3, I. 43; formulations p. 5, I. 26 to 60;

(DC-05): U.S. Pat. No. 6,368,360, wherein directed dyes (col. 4, I. 1 to col. 6, I. 31) and oxidizing agents (col. 6, I. 37-39) are disclosed; formulations col. 7, I. 47 to col. 9, I. 4;

(DC-06): EP 1 166 752, wherein cationic dyes (p. 3, I. 22-p. 4, I. 15) and anionic UV-absorbers (p. 4, I. 27-30) are disclosed; formulations p. 7, I. 50-p. 9, I. 56;

(DC-07): EP 998,908, wherein oxidation dyeings comprising a cationic direct dye and pyra-zolo-[1,5-a]-pyrimidines (p. 2, I. 48-p. 4, I. 1) are disclosed; dyeing formulations p. 47, I. 25 to p. 50, I. 29;

(DC-08): FR-2788432, wherein combinations of cationic dyes with Arianors are disclosed, especially p. 53, I. 1 to p. 63, I. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, I. 16 to p. 3, I. 16; dyeing formulations on p. 53, I. 1 to p. 63, I. 23;

(DC-09): DE-A-19 713 698, wherein the combinations of direct dyes and permanent-wave fixing comprising an oxidation agent, an oxidation dye and a direct dye are disclosed; especially p. 4, I. 65 to p. 5, I. 59;

(DC-10): EP 850 638, wherein developer compounds and oxidizing agents are disclosed; especially p. 2, I. 27 to p. 7, I. 46 and preferably p. 7, I. 20 to p. 9, I. 26; dyeing formulations p. 2, I. 3-12 and I. 30 to p. 14, and p. 2, I. 35-p. 30, I. 20; preferably p. 30, I. 25-p. 32, I. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, I. 40-col. 7, I. 14), optionally dispersed in an organic pulverulent excipient and/or a mineral pulverulent excipient, and a composition (C) containing one or more oxidizing agents are disclosed; formulations col. 8, I. 60-col. 9, I. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, I. 17-col. 13, I. 65; dyeing formulations in col. 2, I. 16 to col. 25, I. 55, a multi-compartment dyeing device is described in col. 26, I. 13-24;

(DC-13): WO 99/20235, wherein compositions of at least one cationic dye and at least one nitrated benzene dye with cationic direct dyes and nitro benzene direct dyes are described; on p. 2, I. 1 to p. 7, I. 9, and p. 39, I. 1 to p. 40 I. 11, preferably p. 8, I. 12 to p. 25 I. 6, p. 26, I. 7 to p. 30, I. 15; p. 1, I. 25 to p. 8, I. 5 p. 30, I. 17 to p. 34 I. 25, p. 8, I. 12 to p. 25 I. 6, p. 35, I. 21 to 27, especially on p. 36, I. 1 to p. 37;

(DC-14): WO 99/20234, wherein compositions comprising at least one direct cationic dye and at least one autooxidisable dye, especially benzene, indol and indol. derivatives are described, preferably direct dyes on p. 2, I. 19 to p. 26, I. 4, and autooxidisable dyes as disclosed especially on p. 26, I. 10 to p. 28, I. 15; dyeing formulations especially on p. 34, I. 5 to p. 35, Ii 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, I. 41 to p. 7, I. 52, dyeing formulations p. 19, I. 50-p. 22, I. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, I. 50 to p. 8, I. 44 are disclosed; dyeing formulations p. 21, I. 30-p. 22, I. 57;

(DC-17): WO 99/48856, wherein oxidation dyeing compositions comprising cationic couplers are disclosed, especially p. 9, I. 16-p. 13, I. 8, and p. 11, I. 20-p. 12, I. 13; dyeing formulations p. 36, I. 7-p. 39, I. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptides, aromatic hydroxy compounds, and/or at least one CH-active compound are disclosed p. 3, I. 42-p. 5 I. 25; dyeing formulations p. 8, I. 25-p. 9, I. 61.

In the dye combinations disclosed in the references (DC-01-DC-18) above, the dyes of formula (1) according to the present invention may be added to the dye combinations or dyeing formulations or may be replaced with at least one dye of formula (1).

The present invention also relates to formulations, which are used for the dyeing of organic materials, preferably keratin-containing fibers, and most preferably human hair, comprising at least one dye of formula (1).

Preferably the dyes of formula (1) are incorporated into the composition for treating organic material, preferably for dyeing in amounts of 0.001-5% b.w. (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

One preferred embodiment of the present invention relates to the formulation of dyes, wherein the dyes of formula (1) are in powder form.

Powder formulations are preferably used if stability and/or solubility problems as for example described in DE 197 13 698, p. 2, I. 26 to 54 and p. 3, I. 51 to p. 4, I. 25, and p. 4, I. 41 to p. 5 I. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts, for example emulsifiers may be present in the dyeing compositions in concentrations from 0.5 to 30% b.w. and thickeners in concentrations from 0.1 to 25% b.w. of the total dyeing composition.

Further carriers for dying compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

The dyes of formula (1) may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuavents are preferably used in the hair dyeing compositions of the present invention: non-ionic polymers, cationic polymers, acrylamide/dimethyldiallylammonium chloride copolymers, quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value; panthenol, pantothenic acid, allantoin, pyrrolidonecarboxylic acids and salts thereof, plant extracts and vitamins; cholesterol; light stabilisers and UV absorbers, consistency regulators, fats and waxes, fatty alkanolamides, polyethylene glycols and polypropylene glycols, complexing agents, swelling and penetration substances, opacifiers, such as latex; pearlising agents, propellants, antioxidants; sugar-containing polymers, quaternary ammonium salts, or bacteria inhibiting agents.

The dyeing compositions according to the present invention generally comprise at least one surfactant. Suitable surfactants are zwitterionic or ampholytic, or more preferably anionic, non-ionic and/or cationic surfactants.

Suitable anionic surfactants are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one —COO$^-$ or —SO$_3^-$ group in the molecule are terminated zwitterionic surfactants. Preference is given the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazol. having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a polyalkylene glycol ether group or a combination of polyol and polyglycol ether groups.

Examples of cationic surfactants that can be used in the dyeing compositions according to the invention are especially quaternary ammonium compounds.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

A further preferred embodiment of the present invention relates to a method of treating keratin-containing fibers with sulfide dyes of formula (1).

The method comprises treating the hair in the presence of a reduction agent.

Preferred reduction agents are for example thioglycol acid or salts thereof, gycerine monothioglycolat, cystein, 2-mercaptopropionic acid, 2-mercaptoethylamine, thiolactic acid, thioglycerine, sodium sulfite, dithionithe, ammonium sulfite, sodium bisulfite, sodium metabisulfite or hydrochinon.

In addition, the present invention relates to a method of
a. treating the keratin-containing fibers with a compound of formula (1),
b. wearing the coloured hair for the desired period of time,
c. removing the colour applied in step a) from hair by contacting the hair with an aqueous based colour removal composition containing a reduction agent capable of disrupting the S-S-bonds between the dye molecule and the hair fiber surface to cause the dye molecule to become disassociated from the hair fiber.

Further, the present invention concerns a process, comprising treating the hair with
a. a reduction agent, and
b. at least a single sulfide dye of formula (1) as defined above, and optionally
c. with an oxidizing agent.

The sequence of the reaction steps is generally not important, the reduction agent can be applied first or in a final step.
Preferred is a process, which comprises treating the hair
$a_1$) with at least one single dye of formula (1), and
$b_1$) then with a reduction agent; or
a process, which comprises contacting hair
a2) with a reduction agent and
$b_2$) then with at least one single sulfide dye of formula (1) as defined above.

In the present invention preferred is further a process, which comprises contacting hair
a) with a reduction agent,
b) then with at least one dye of formula (1), and
c) then with an oxidizing agent.

A further process of the present invention comprises contacting hair
a) with at least one single dye of formula (1), and
b) then with a reduction agent, and
c) then with an oxidizing agent.

Usually, the oxidizing agent is applied together with an acid or a base.

The acid is for example citric acid, phosphoric acid or tartrate acid.

The base is for example sodium hydroxide, ammonia or monoethanolamine.

Usually, the dyeing compositions are applied to the keratin-containing fiber in an amount of from 50 to 100 g.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1), a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

In general, the oxidizing agent containing composition is left on the fiber for 0 to 15 minutes, in particular for 0 to 5 minutes at 15 to 45° C., usually in amounts of 30 to 200 g.

Oxidizing agents are for example persulfate or dilute hydrogen peroxide solutions, hydrogen peroxide emulsions or hydrogen peroxide gels, alkali, earth metal peroxides, organic per-oxides, such as urea peroxides, melamine peroxides, or alkalimetalbromat fixations are also applicable if a shading powder on the basis of semi-permanent, direct hair dyes is used.

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula $$\begin{array}{c} R_3 \\ \diagdown \\ R_4 \end{array} N-R-N \begin{array}{c} R_5, \\ \diagup \\ R_6 \end{array}$$

wherein

R is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, l. 19 to l. 27.

Furthermore, the present invention relates to a process of dyeing of keratin-containing fibers of the dyes of formula (1) with autooxidable compounds and optionally further dyes.

Furthermore, the present invention relates to a process for dyeing keratin-containing fibers with the dyes of formula (1) and at least one acid dye.

The following Examples serve to illustrate the processes for dyeing without limiting the processes thereto. Unless specified otherwise, parts and percentages relate to weight. The amounts of dye specified are relative to the material being coloured.

T, s, d, q and J, wherein t is a triplett, s is singulett, d is duplett, q is a quartett, and J is a coupling constant, define the NMRspectra values.

EXAMPLES A

Process of Preparation

EXAMPLE A1

(101)

12.4 g 4-fluoroaniline are added to a stirred solution of 25 ml water and 25 ml of 32% hydrochloric acid at 295 K. The reaction mixture is cooled to 273 K and 19 ml of a 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide paper) further sodium nitrite solution is added. The remaining excess of nitrite is reduced with sulfamic acid. The obtained diazo solution is dropped to a 273 K cold solution of 7.4 g imidazole in 30 ml water, whereby the pH of the solution is maintained in the range of pH 10 to 11 by adding 36% of a sodium hydroxide solution. After completing the diazo addition the obtained suspension is warmed up to 295 K, the pH is adjusted to 10.5 with 36% sodium hydroxide solution. After stirring for one hour at this pH and temperature the suspension is filtered off and washed twice with 50 ml water to obtain 55 g of a humid product, which is suspended in 200 ml water and 3 weight equivalents dimethyl sulfate and sodium hydroxide are simultaneously added for maintaining the pH at 10-10.3 and the temperature at 298-303K.

The reaction is allowed to stand for one more hour to finish the hydrolysis of excess of dimethyl sulfate.

100 g sodium chloride and 50 g potassium chloride are added at 273K and allowed to stand for 16 hours. The product is separated by filtration and washed with a cold solution of sodium/potassium chloride. About 20 g of the compound of formula

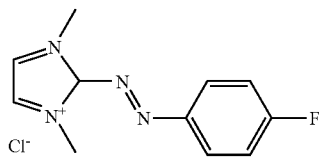

(101a)

are obtained 6.9 g of cisteamine dihydrochloride are added at 293 K under nitrogen atmosphere to 20 g of the compound of formula (101a) in 120 g isopropanol and 24 g triethylamine. The temperature is raised to 333 K and the reaction mixture is stirred at this temperature during 25 hours. The reaction mass is stirred for 4 hours while the temperature is decreased to 295 K. The reaction mass is filtered off and the filter residue washed with 45 ml of isopropanol and again filtered. 300 ml water are added to the humid filter residue and the mixture is stirred for 3 hours at 353 K. Then the temperature is decreased to 295 K and the mixture filtered off. The filter residue is washed with 100 ml water, filtered and dried in vacuum to obtain 16 g of compound of formula (101).

$^1$H-NMR Data in deuterated methanol (128 scans)/360 MHz:

| 7.924 | d | 7.3 | 3.95 | phenylen |
| 7.5109 | S | | 3.82 | imidazol |
| 6.857 | d | 7.8 | 3.96 | phenylen |
| 4.038 | s | | 12.06 | dimethyl |
| 3.595 | t | | 3.982 | methylen |
| 2.925 | t | | 4.00 | methylen |

EXAMPLE A2

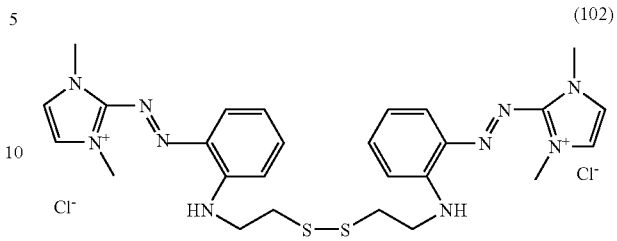

(102)

12.4 g 2-fluoroaniline are added to a stirred solution of 25 ml water and 25 ml of 32% hydrochloric acid at 295 K. The reaction mixture is cooled to 273 K and 19 ml 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide/starch paper) further amounts of sodium nitrite solution are added. Then the remaining excess of nitrite is destroyed with sulfamic acid. The obtained diazo solution is dropped to a 273 K cold solution of 7.4 g imidazole in 30 ml water, whereby the pH of the solution is maintained in the range of pH 10 to 11 by adding 36% sodium hydroxide solution. After completing the diazo addition the obtained suspension is warmed up to 295 K and the pH is adjusted to 10.5 with 36% sodium hydroxide solution. After stirring for one hour at this pH and temperature the suspension is filtered off and then washed twice with 50 ml water to obtain 55 g of the humid product, which is suspended in 500 ml water. 0.3 mol dimethyl sulfate and sodium hydroxide are simultaneously added for maintaining the pH in the range of 10-10.3 and the temperature at 298-303K. The reaction mixture is hold for one hour. Then the water is evaporated.

About 40 g humid solid, which gives 27 g of dryed product of the formula

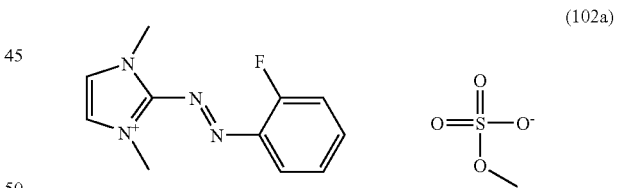

(102a)

is obtained

The product is characterized by $^1$H-NMR Data in deuterated methanol (128 scans)/360 MHz:

| 8.002 | ddd | J = 7.6; J = 7.5; j = 1.4 | 1.029 | |
| 7.893 | s | | 2.00 | imidazol |
| 7.812 | m | J = 8.6, J = 6.7, J = 1.4 | 0.99 | |
| 7.505 | ddd | J = 8.6 | 1.06 | |
| 7.436 | t | | 0.949 | |
| 4.211 | s | | 5.78 | dimethyl of imidazol |
| 3.69 | s | | 4.01 | methy of monomethylsulfate |

11 g cisteamin chlorohydrate are added to 27 g of compound of formula (102a) in 20 g triethylamine and 120 g isopropanol under nitrogen atmosphere at 293 K, The temperature is raised to 333 K. The reaction mixture is stirred for 28 hours at this temperature. Then the reaction mass is stirred for 4 hours while the temperature is decreased to 295 K. The reaction mass is filtered off and the filter residue washed with 45 ml isopropanol and dried in vacuum to obtain 17.6 g of product f formula (102).

The product is characterized by $^1$H-NMR Data in deuterated methanol (128 scans)/360 MHz:

| 7.78 | dd | J = 8.6; J = 1.4 | 2.07 | |
|------|----|----|------|------|
| 7.620 | s | | 4.00 | imidazol |
| 7.498 | m | J = 8.6; J = 6.7 J = 1.4 | 1.968 | |
| 7.083 | d | J = 8.6 | 1.875 | |
| 6.831 | m | | 1.938 | |
| 4.057 | s | | 12.08 | dimethyl of dmidazol |
| 3.846 | t | 6 | 3.75 | methylene |
| 3.69 | s | | 4.01 | methy of monomethylsulfate |
| 3.109 | t | 6 | 3.95 | methylene |

EXAMPLE A3

(103)

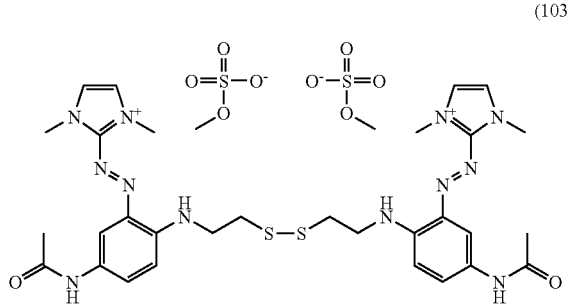

100 g 4-fluoro-3nitroanilin are added to a stirred mass of 80 g methanol and heated to 333 K. 0.1 ml sulfuric acid and 90 ml of acetic anhydride are added during 15 minutes. Heating and boiling are continued for 15 minutes. Then the reaction mixture is cooled slowly to 273 K with stirring. At the final temperature stirring is continued for 30, minutes, then the suspension is filtered off, washed with cold methanol, dryed in the vacuum dryer getting 114 g acetyl derivative which is worked up further. The acetyl derivative is solved in 520 ml ethanol and continuously added to 130 g iron in 35 ml concentrated hydrochloric acid and 220 ml water at 363K during 1 hour. The temperature drops to 353 K. The reaction mixture is stirred for further 3 hours. The hot mass is separated through filtration the residue washed with 100 ml ethanol. The filtrate and wash solution are cooled to 380 K with mixing, when crystallization of the product takes place. The product is separated by filtration, washed with cold ethanol and dryed in a vacuum dryer.

The dried material is dissolved in 132 ml water and 110 ml of 32% hydrochloric acid at 295 K. The reaction mixture is cooled to 273 K and 86.4 g 36% sodium nitrite solution are dropped at such a rate that the temperature of the mixture is maintained in the range of 273 to 276 K. The mixture is further stirred for one hour. If no excess of nitrite is detected during one hour (detection by using a potassium iodide/starch paper) further amounts of sodium nitrite solution are added. After this one hour the remaining excess of nitrite is destroyed with sulfamic acid. Then the obtained diazo solution is dropped to a 273 K cold solution of 33.4 g imidazole in 130 ml water, whereby the pH of the solution is maintained in the range of pH 10 to 11 by adding 36% of a sodium hydroxide solution. After completing the diazo addition, the obtained suspension is warmed up to 295 K and the pH is adjusted to 10.5 with 36% sodium hydroxide solution. After stirring for one hour at this pH and temperature the suspension is filtered off and then washed twice with 100 ml water to obtain 200 g of the humid product. The filtercake from the previous step is suspended in water and 3 weight equivalents dimethylsulfate and sodium hydroxide are simultaneously added for maintaining the pH in the range of 10-10.3 and the temperature at 300 K. Then the reaction mixture is hold for one more hour to finish the hydrolysis of excess of dimethylsulfate. Then the suspension is separated by filtration. About 240 g of a humid solid which gives 140 g dryed product of formula (103a)

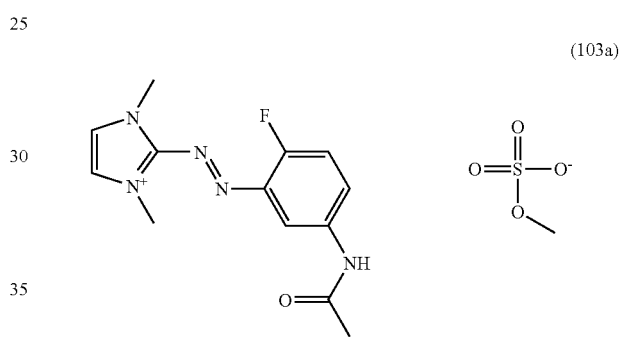

is obtained.

38.8 g of the product of formula (103a) are added to a stirred mixture of 10.6 g of cisteamin chlorohydrate in 15 g triethylamine and 70 g acetonitrile under nitrogen atmosphere at 293 K. The temperature is maintained at 273 K. The reaction mixture is stirred for 20 hours at this temperature. The reaction mass is filtered off and the filter residue washed with 45 ml of acetonitrile and dried in vacuum to obtain 42 g of product of formula (103).

The product is characterized by $^1$H-NMR Data in deuterated methanol (128 scans)/360 MHz:

| 8.11 | d, J = 1.7 | 2.00 | orto |
|------|----|------|------|
| 7.6 | d, d, J = 8.6; J = 1.4 | 6.06 | para |
| 7.57 | s | | imidazol |
| 7.00 | d, J = 9.5 | 2.04 | meta |
| 4.03 | s | 12.22 | methyl |
| 3.860 | t | 3.89 | methylene |
| 3.69 | s | 6.44 | methylsulfate |
| 3.109 | t | 4.28 | methylene |
| 2.14 | a | 6.22 | acetyl |

EXAMPLE A4

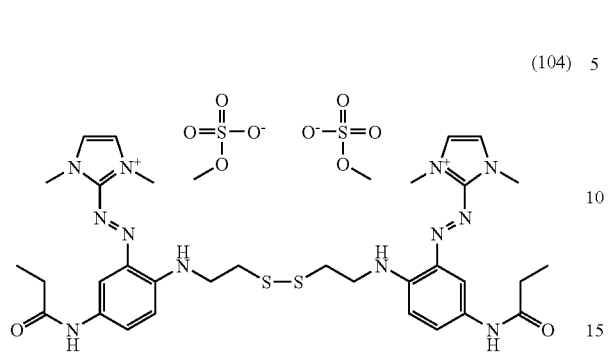

(104)

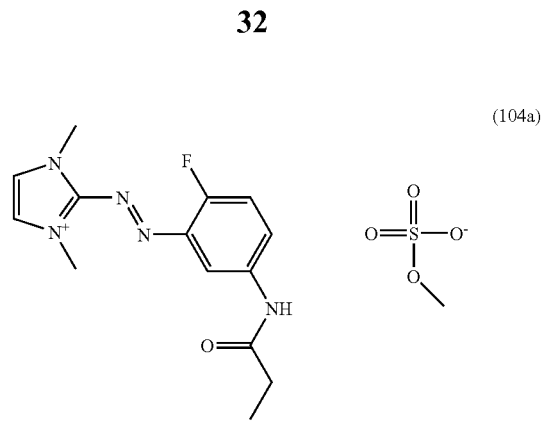

(104a)

100 g 4-fluoro-3-nitro-anilin is added to a stirred mass of 80 g methanol, heated to 333 K, 0.1 ml sulfuric acid added, and then 90 ml of propionic anhydride during 15 minutes. Then heating and boiling is continued for 15 minutes. Then the reaction mixture is cooled slowly to 273 K with stirring. At the final temperature stirring is continued for 30 minutes, then the suspension is filtered, washed with cold methanol, dryed in the vacuum dryer getting 114 g acetyl derivative which is worked up further. Then, the acetyl derivative is solved in 520 ml ethanol and continuously added to 130 g iron in 35 ml concentrated chlorhidric acid and 220 ml water at 363K during 1 hour. The temperature drops to 353 K. The reaction mixture is stirred for further 3 hours. The hot mass is separated through filtration, the residue washed with 100 ml ethanol. The filtrate and wash solution is cooled to 380 K with mixing; when crystallization of the product takes place. The product is separated by filtration, washed with cold ethanol and dryad in a vacuum dryer.

The dried material is dissolved in 132 ml water and 110 ml of 32% hydrochloric acid at 295 K. Then the reaction mixture is cooled to 273 K and 86.4 g 36% sodium nitrite solution is dropped at such a rate that the temperature of the mixture is maintained in the range of 273 to 276 K. After the addition of the sodium nitrite solution, the mixture is stirred for one hour. If no excess of nitrite is detected during one hour (detection by using a potassium iodide/starch paper), further amounts of sodium nitrite solution is added. After this one hour the remaining excess of nitrite is destroyed with sulfamic acid. Then, the obtained diazo solution is dropped to a 273 K cold solution of 33.4 g imidazole in 130 ml water, whereby the pH of the solution is maintained in the range of pH 10 to 11 by adding 36% sodium hydroxide solution. After completing the diazo addition, the obtained suspension is warmed up to 295 K, the pH is adjusted to 10.5 with 36% sodium hydroxide solution. After one hour stirring at this pH and temperature, the suspension is filtrated and then washed twice with 100 ml water to obtain 200 g of the humid product Then, the filtercake from the previous step is suspended in water and 3 weight equivalents dimethylsulphate and sodium hydroxide simultaneously added for maintaining the pH in the range of 10-10.3 and the temperature at 300 K. Then, the reaction mixture is hold for one more hour, to finish the hydrolysis of excess of dimethylsulphate. Then, the suspension is separated by filtration. About 240 g humid solid, which gives 140 g dryed product of formula Characterization by $^1$H-NMR Data in Deuterated Methanol (128 scans)/360 MHz

| | | | Residue of compound |
|---|---|---|---|
| 8.415 | d, J = 2.7; 6.6 | 0.95 | ortho coupling |
| 7.889 | s | 2.00 | imidazol |
| 7.820 | d, d, d; | 0.98 | para coupling |
| 7.468 | d, d J = 9.5: 9.5 | 1.04 | meta coupling |
| 4.203 | s | 6.22 | methyl |
| 3.69 | s | 3.00 | methylsulfat |
| 2.175 | q | 2.22 | propionyl |
| 1.20 | t | 3.28 | propionyl |

38.8 g of the product of formula (104a) are added under nitrogen atmosphere at 293 K to a stirred mixture of 10.6 g of cisteamin chlorohydrate in 15 g triethylamine and 70 g acetonitrile. The temperature is maintained at 273 K. The reaction mixture is stirred for 20 hours at this temperature. The reaction mass is filtered off and the filter residue is washed with 45 ml of acetonitrile and dried in vacuum to obtain 32.6 g of product of formula (104). Characterization by $^1$H-NMR Data in deuterated methanol (128 scans)/360 MHz

| | | | Residue of compound (104) |
|---|---|---|---|
| 8.11 | d, J = 1.7 | 2.00 | ortho coupling |
| 7.6 overlaid | d, d, J = 8.6; J = 1.4 | 6.06 | para coupling |
| 7.57 | s | | imidazol |
| 7.00 | d, j = 9.5 | 2.04 | meta coupling |
| 4.03 | s | 12.22 | methyl |
| 3.860 | t | 3.89 | methylene |
| 3.69 | s | 6.44 | methylsulfate |
| 3.109 | t | 4.28 | methylene |
| 2.14 | q | 4.22 | propionyl |
| 1.20 | t | 6.27 | propionyl |

EXAMPLE A5

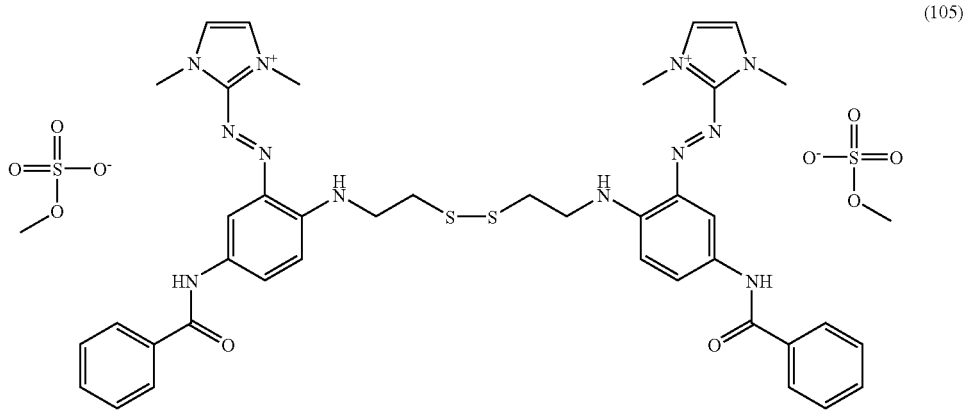

(105)

100 g 4-fluoro-3-nitro-anilin are added to a stirred mass of 80 g methanol and heated to 333 K. 0.1 ml sulfuric acid and 90 ml of benzoyl chloride are added during 15 minutes. Heating and boiling is continued for 15 minutes. The reaction mixture is cooled slowly to 273 K with stirring and continued for 30 minutes. The suspension is filtered off, washed with cold methanol, dryed in the vacuum dryer getting 114 g acetyl derivative which is worked up further. The acetyl derivative is dissolved in 520 ml ethanol and continuously added to 130 g iron in 35 ml concentrated chlorhidric acid and 220 ml water at 363K during 1 hour. The temperature drops to 353 K. The reaction mixture is stirred for further 3 hours. The hot mass is separated through filtration, the residue washed with 100 ml ethanol. The filtrate and wash solution are cooled to 380 K with mixing when crystallization of the product takes place. The product is separated by filtration, washed with cold ethanol and dryed in a vacuum dryer. The dried material is dissolved in 132 ml water and 110 ml of 32% hydrochloric acid at 295 K. Then the reaction mixture is cooled to 273 K and 86.4 g of a 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide/starch paper) further amounts of sodium nitrite solution are added. The remaining excess of nitrite is destroyed with sulfamic acid. Then the obtained diazo solution is dropped to a 273 K cold solution of 33.4 g imidazole in 130 ml water, whereby the pH of the solution is maintained in the range of pH 10 to 11 by adding 36% of a sodium hydroxide solution. After completion of the diazo addition the obtained suspension is warmed up to 295 K, the pH adjusted to 10.5 with 36% sodium hydroxide solution. After stirring for one hour at this pH and temperature the suspension is filtered off and then washed twice with 100 ml water to obtain 200 g of the humid product. Then the filtercake from the previous step is suspended in water and 3 weight equivalents dimethylsulfate and sodium hydroxide simultaneously added for maintaining the pH in the range of 10-10.3 and the temperature at 300 K. Then the reaction mixture is hold for one more hour to finish the hydrolysis of excess of dimethylsulfate. Then, the suspension is separated by filtration.

About 240 g of a humid solid, which gives 140 g dry product of the following formula

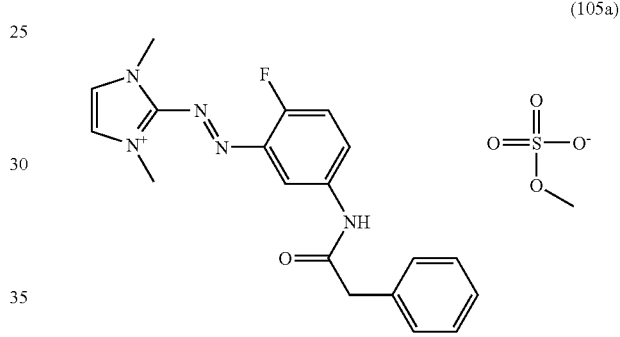

(105a)

is obtained

Characterization by $^1$H-NMR Data in Deuterated Methanol (128 scans)/360 MHz

|  |  |  | Residue of compound |
|---|---|---|---|
| 8.415 | D, j = 2.7; 6.6 | 0.95 | ortho coupling |
| 7.889 | s | 2.00 | Imidazol |
| 7.820 | d, d, d; | 0.98 | para coupling |
| 7.468 | D, d j = 9.5: 9.5 | 1.04 | meta coupling |
| 4.203 | s | 6.22 | methyl |
| 3.69 | s | 3.00 | methylsulfat |

48 g of the compound of formula (105a) are added to a stirred mixture of 11.6 g of cisteamin chlorhydrate in 15 g triethylamine and 70 g acetonitrile under nitrogen atmosphere at 293 K. Then the temperature is maintained at 273 K. The reaction mixture is stirred for 20 hours at this temperature. The reaction mass is filtered off and the filter residue is washed with 45 ml acetonitrile and dried in vacuum to obtain 42.6 g of the compound of formula (105). Characterization by $^1$H-NMR Data in deuterated methanol (128 scans)/360 MHz:

|  |  |  | Residue of compound |
|---|---|---|---|
| 8.11 | d, j = 1.7 | 2.00 | ortho coupling |
| 7.6 overlaid | d, d, J = 8.6; j = 1.4 | 6.06 | para coupling |

| | | | | |
|---|---|---|---|---|
| | | -continued | | |
| | | | | Residue of compound |
| 7.57 | s | | | Imidazol coupling |
| 7.00 | d, j = 9.5 | | 2.04 | meta coupling |
| 4.03 | s | | 12.22 | methyl |
| 3.860 | t | | 3.89 | methylene |
| 3.69 | s | | 6.44 | methylsulfat |
| 3.109 | t | | 4.28 | methylene |

EXAMPLE A6

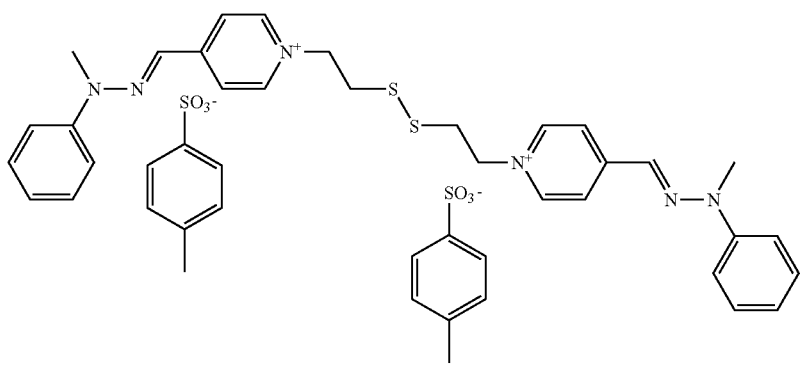

(106)

1. Formation of the Hydrazone: 14 g sulfuric acid are added to 42 g of water and cooled to 293K. 24 g of N-methyl-phenyl hydrazine (100%) are added with stirring. 24.5 g of 4-pyridine-aldehyde are dropped in during 15 minutes and stirring is continued for 1 hour. The pH is raised to 2.2 by adding a solution of 36% sodium hydroxide in water. 2.7 g sodium chloride are added at the 333K. Stirring is continued at this temperature for one hour. The slurry is separated by filtration; the filter cake is dried at 343K in vacuum to yield 42 g of an orange powder.

2. Alkylating agent: A mixture of 15.4 g of 2.2-dithiodiethanol in 100 ml chloroform and 24.1 g pyridine are cooled with stirring at 273K and then 41.0 g of tosyl chloride are added in small amounts, maintaining the temperature.

After completion of the addition the mixture is left over night in the refrigerator. The reaction mixture is mixed with a water/hydrochloric acid/ice slurry. The phases are separated, washed with water and dried. The obtained solution of toluenesulfonate diester is used in the 3. step.

3. Alkylation: The foregoing hydrazone is dissolved by stirring with the equivalent amount of diester solution. Temperature is raised to 334K which is maintained during the following 48 hours. Crystals separated in the slurry are filtered off. The product is washed with 50 ml chloroform and dried in vacuum to obtain 59 g of an orange solid product. The product is recrystallized twice from methanol.

Characterization by $^1$H-NMR data in Deuterated Methanol (32 scans)/360 MHz:

| | | | | |
|---|---|---|---|---|
| | | | | Residues of the compound |
| 8.632 | d | 6.8 | 4.00 | pyridinyl |
| 8.070 | d | 6.7 | 3.98 | pyridinyl |
| 7.701 | d | 7.0 | 3.74 | tosylate |
| 7.648 | s | | 2.04 | hydrazon |

| | | | | |
|---|---|---|---|---|
| | | -continued | | |
| | | | | Residues of the compound |
| 7.528 | d | 6.1 | 3.967 | phenyl |
| 7.410 | t | 6.1 | 4.025 | phenyl |
| 7.195 | t | 6.6 | 3.846 | tosylate |
| 7.148 | t | 6.4 | 2.05 | phenyl |
| 4.78 | t | 6.77 | 4.00 | ethylene |
| 3.625 | s | | 6.05 | mehydrazon |
| 3.385 | t | 6.55 | 4.087 | ethylene |
| 2.326 | s | | 5.90 | tosylate |

EXAMPLE A7

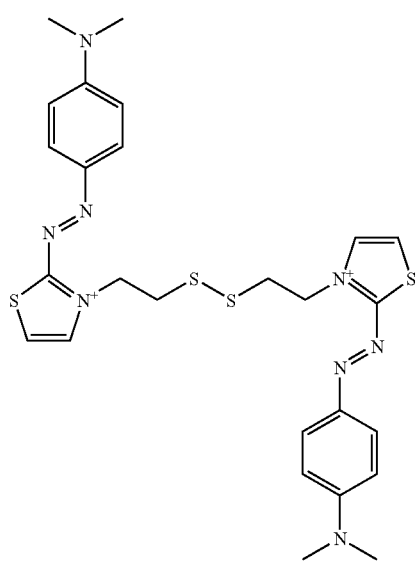

(107)

1. Monoazo: 50.0 of g 2-amino-thiazol are added to a stirred solution of 135 ml 60% sulfuric acid at 293-310 K. Then, the reaction mixture is cooled to 273 K and 81 ml of a 40% nitrosilsulfuric acid are dropped in at such a rate that the temperature of the mixture is maintained in the range of 273 to 276 K by cooling. After the addition the mixture is stirred for four hours. The solution is dropped to a well-stirred water ice mixture (400 g) containing 2,5 g amidosulfuric acid. To the obtained diazo solution (at 273 K ice added if need) 60,5 g dimethylaniline are dropped. Then the pH of the solution is raised to the range of 5 to 6 by adding 36% sodium hydroxide solution. After one hour stirring at this pH and temperature the suspension is filtered off and then washed twice with 50 ml water to obtain 155 g of the humid product. After drying 100 monoazo dye is obtained.

2. Alkylating agent: A mixture of 15.4 g of 2,2-dithiodiethanol in 100 ml chloroform and 24, 1 g pyridine are cooled with stirring to 273 K and then 41.0 g of tosyl chloride are added in small amounts maintaining the temperature.

After completion of the addition the mixture is left over night in the refrigerator. The reaction mixture is mixed with a water/hydrochloric acid/ice slurry, the phases are separated, washed with water and dried. The obtained solution of toluenesulfonate diester is used in the following step 3. Alkylation: The foregoing monoazo is dissolved by stirring into the diester solution. Temperature is raised to 333K. The temperature is maintained at 333K during the following 60 hours. Crystals separated in the slurry are filtered off. The product is washed with 50 ml of chloroform and dried in vacuum to obtain 59 g of a dark violet solid product. The product is recrystallized twice from methanol.

Characterization by $^1$H-NMR Data in Deuterated Methanol (128 scans)/360 MHz:

|       |   |           |       | Residues of the compound |
|-------|---|-----------|-------|--------------------------|
| 8.095 | d | J = 8.6;  | 2.07  |                          |
| 7.867 | d | J = 4.2   | 2.00  | thiazol                  |
| 7.696 | d | overlaid  | 6     | phenylene                |
| 7.470 | d | J = 4.3   | 1.968 | thiazol                  |
| 7.217 | d | J = 8.6   | 4.00  | tosyl                    |
| 7.083 | d | J = 8.6   | 3.97  | phenylene                |
| 4.856 | t | 5.6       | 4.08  | methylene                |
| 3.419 | s |           | 12    | methyl                   |
| 3.139 | t | 5.6       | 4.01  | methylen                 |
| 2.309 | s |           | 6.00  | Methyl                   |

EXAMPLE A8

(108)

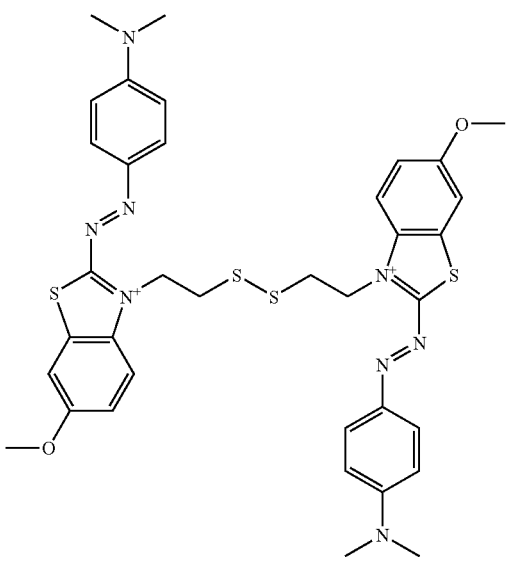

Monoazo Synthesis 90.0 g 2-amino-6-methoxy-benzothiazol are added to a stirred solution of 135 ml 60% sulfuric acid at 293 K. The reaction mixture is cooled to 273 K and 81 ml of a 40% nitrosylsulfuric acid are dropped at such a rate that the temperature of the mixture is maintained in the range of 273 to 276 K with cooling and stirred for four hours. The solution is dropped to a well-stirred water ice mixture (400 g) containing 2.5 g amidosulfuric acid. 60,5 g dimethylaniline are dropped to the obtained diazo solution (at 273 K ice added if need). The pH of the solution is adjusted between 5 and 6 by adding 36% sodium hydroxide solution. After stirring for one hour at this pH and temperature the suspension is filtered off and washed twice with 50 ml water to obtain 255 g of the humid product. After drying 151 monoazo dye is obtained.

2. Alkylating agent: A mixture of 21.4 g of 2.2-dithiodiethanol in 100 ml chloroform and 24-0.1 g pyridine are cooled with stirring to 273K and then 41.0 g of mesyl anhydride are added in small amounts under constant temperature.

After completion of the addition the mixture is left over night in the refrigerator to finish the reaction. The reaction mixture is mixed with a water/hydrochloric acid/ice slurry, the phases are separated, washed with water and dried. The obtained solution of methanesulfonate diester is used in the following step 3. Alkylation: Two equivalents of the foregoing monoazo are dissolved by stirring into the diester solution. Temperature was raised to 334K. The temperature was maintained at 334K during the following 80 hours. Crystals separated in the slurry are filtered off. The product is washed with 50 ml of chloroform and dried in vacuum to obtain 80 g of a dark violet solid product. The product is recrystallized twice from methanol.

Characterization by $^1$H-NMR in Deuterated Methanol (128 scans)/360 MHz:

|        |   |     |       | Residues of compound |
|--------|---|-----|-------|----------------------|
| 7.924  | d | 7.3 | 3.95  | phenylene            |
| 7.5109 | s |     | 3.82  | imidazole            |
| 6.857  | d | 7.8 | 3.96  | phenylene            |
| 4.038  | s |     | 12.06 | dimethyl             |
| 3.595  | t |     | 3.982 | methylene            |
| 2.925  | t |     | 4.00  | methylene            |

EXAMPLE A9

(109)

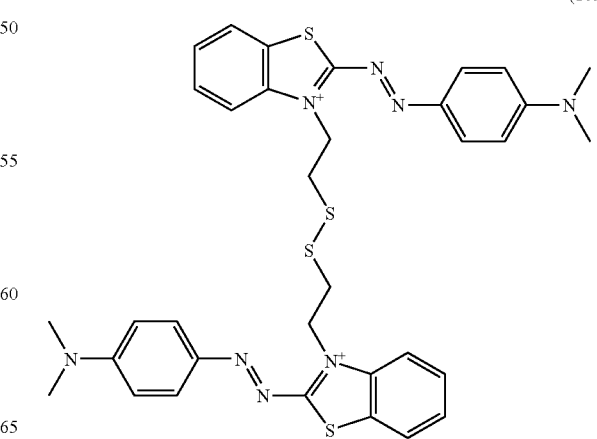

Same preparation process as described in example A8, but with the difference that 2-amino-benzothiazol instead of 2-amino-6-methoxy-benzothiazol is used.

EXAMPLE A10

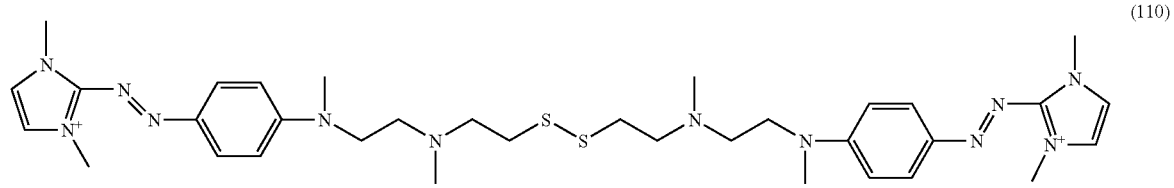
(110)

19.9 g of N,N'-dimethyl-ethylendiamine are added with stirring to 120 g acetonitrile and compound of the formula of formula (101a) at 293 K under nitrogen atmosphere. The temperature is raised to 333 K while the viscosity of the reaction mixture decreases. The reaction mixture is stirred at this temperature during 25 hours. Then the reaction mass is stirred for 4 hours while the temperature is decreased to 295 K. The reaction mass is filtered off and the filter residue is washed with 45 ml of acetonitrile. Then the material is dried in vacuum to obtain 16 g of product.

2. Alkylating agent: A mixture of 15.4 g of 2.2-dithiodi-ethanol in 100 ml chloroform and 24.1 g pyridine are cooled with stirring to 273K and then 41.0 g of tosyl chloride are added in small amounts under constant temperature.

After completion of the addition the mixture is left over night in the refrigerator. The reaction mixture is mixed with a water/hydrochloric acid/ice slurry, the phases are separated, washed with water and dried. The obtained solution of meth-ane-benzene-sulfonate diester is used in the following step.

3. Alkylation: Stirring into the diester solution in chloroform dissolves two equivalents of the foregoing monoazo. Temperature is raised to 333K. The temperature is maintained at 333K during the following 20 hours. Crystals separated in the slurry are filtrated. The product is washed with 50 ml of chloroform and dried in vacuum to obtain 80 g of a dark solid product. The product is recrystallized twice from methanol.

|  |  |  |  | Residue of compound |
|---|---|---|---|---|
| 7.924 | d | 7.3 | 3.95 | phenylen |
| 7.5109 | s |  | 3.82 | imidazol |
| 6.857 | d | 7.8 | 3.96 | phenylen |
| 4.038 | s |  | 12.06 | dimethyl |
| 3.595 | t |  | 3.982 | methylen |
| 2.925 | t |  | 4.00 | methylen |

EXAMPLE A11

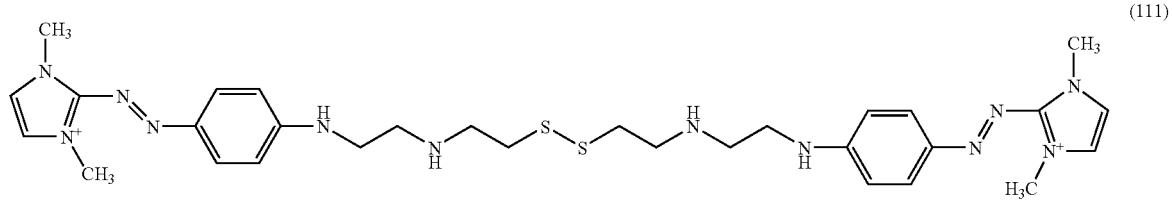
(111)

Same preparation process as described in example A10, but with the difference that ethylendiamine is used instead of N,N'-dimethyl-ethylendiamine.

EXAMPLE A12

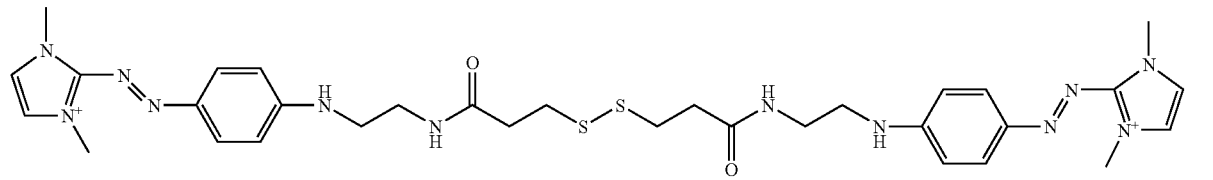
(112)

1. 16.9 g of ethylenediamine are added to the compound of the formula (101a) (prepared in Example A1) and 120 g isopropanol at 293 K under nitrogen atmosphere under stirring. The temperature is raised to 333 K while the viscosity of the reaction mixture decreases. The reaction mixture is stirred at this temperature during 25 hours. Then the reaction mass is stirred for 4 hours while the temperature is decreased to 295 K. The reaction mass is filtered off and the filter residue is washed with 45 ml of isopropanol. Then the filter residue is dried in vacuum to obtain 16 g of the product.

2. Acylating agent: A mixture of 15.4 g of 2,2-dithiodipropionic acid and then 41.0 g of thionyl chloride is warmed to 333 K for 2 hours under constant temperature.

After completion of the addition the mixture is distilled under vacuum.

3. Alkylation: Two equivalents of the foregoing monoazo are dissolved by stirring into the acid chloride solution in chloroform. The temperature is raised to 333K and maintained during the following 48 hours. Crystals separated in the slurry are filtrated. The product is washed with 50 ml of chloroform and dried in vacuum to obtain 80 g of a dark reddish solid product which is recrystallized twice from methanol.

$^1$H-NMR Data in Deuterated Methanol (128 scans)/360 MHz

|  |  |  |  | Residues of compound |
|---|---|---|---|---|
| 7.924 | d | 7.3 | 3.95 | phenylen |
| 7.5109 | s |  | 3.82 | imidazol |
| 6.857 | d | 7.8 | 3.96 | phenylen |
| 4.038 | s |  | 12.06 | dimethyl |
| 3.595 | t |  | 3.982 | methylen |
| 2.925 | t |  | 4.00 | methylen |

EXAMPLE A13

1. Formation of the Hydrazone: 14 g sulfuric acid are added to 42 g of water and cooled to 293K. 25 g of N-methyl-phenyl hydrazine (100%) are added with stirring. 24.0 g of 4-pyridine-aldehyde are dropped in during 15 minutes and stirring is continued for 1 hour. The pH is raised to 2.2 by adding a solution of 36% sodium hydroxide in water. 2.7 g sodium chloride are added at a temperature of 333K and stirred for one more hour at this temperature. The slurry is separated by filtration, the filter cake dried at 343K in vacuum to yield 43 g of an orange powder.

2. Alkylating agent: A solution of 22.5 g of cisteamine dichlorohydrate in water and 31.4 g bromoacetic chloride are cooled with stirring to 273K and then the pH is kept constant by adding NaOH solution in small amounts under constant temperature.

After completion of the addition the mixture is left over night in the refrigerator. The mixture has two phases, which are separated, washed with water and dried.

3. Alkylation: The foregoing hydrazone is dissolved in methanol by stirring with the dibromide solution. The temperature is raised to 60° C. and maintained at 60° C. during the following 24 hours. The crystals separated in the slurry are filtrated. The product is washed with 50 ml of methanol and dried in vacuum to obtain 49 g of an orange solid product. The product is recrystallized twice from methanol.

Characterization by $^1$H-NMR data in Deuterated Methanol (32 scans)/360 MHz:

|  |  |  |  | Residues of the compound |
|---|---|---|---|---|
| 8.442 | d | 6.8 | 4.00 | pyridinyl |
| 8.007 | d | 6.7 | 3.935 | pyridinyl |
| 7.517 | s |  | 2.04 | hydrazon |
| 7.4 | m |  | 8.08 | phenyl |
| 7.162 | t | 6.4 | 1.982 | phenyl |
| 5.235 | s |  | 3.648 | ethylene |
| 3.625 | t | 6.75 | 3.05 | ethylene |
| 3.489 | s |  | 6.23 | methyl |
| 2.947 | t | 6.55 | 4.087 | ethylene |

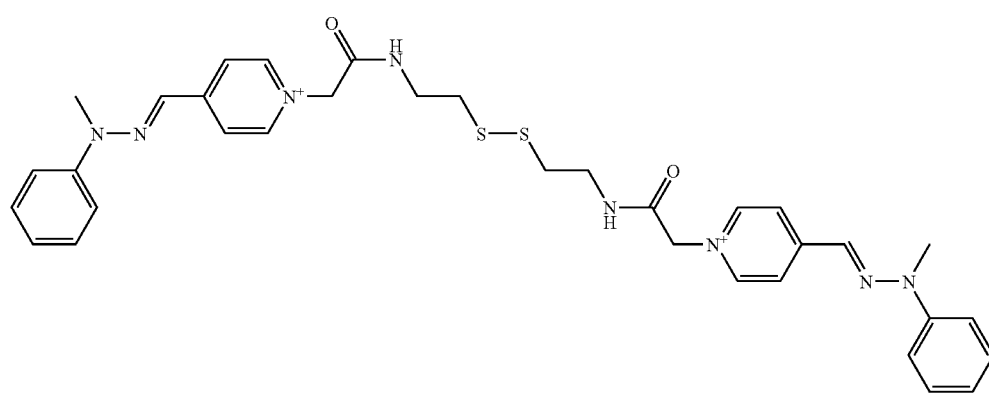

(113)

EXAMPLE A 14

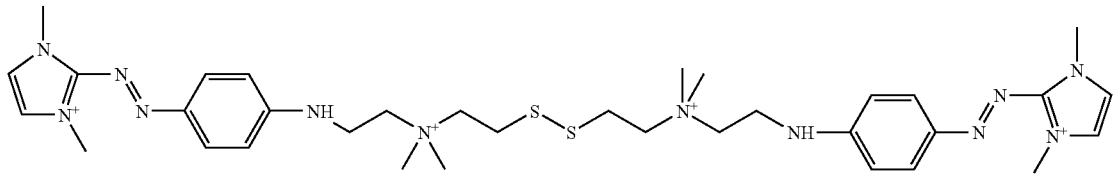

(114)

1. 9.9 g of N,N-dimethyl-ethylendiamine are added to 120 g acetonitrile and to the compound of the formula (101a) (prepared in example A1) at 293 K under nitrogen atmosphere with stirring. The temperature is raised to 333 K while the viscosity of the reaction mixture decreases. The reaction mixture is stirred at this temperature during 25 hours. The reaction mass is stirred for 4 hours while the temperature is decreased to 295 K. The reaction mass is filtered off and the filter residue washed with 45 ml of acetonitrile. Then the material is dried in vacuum to obtain 16 g of product.

2. Alkylating agent: A mixture of 15.4 g of 2.2-dithiodi-ethanol in 100 ml chloroform and 24, 1 g pyridine is cooled with stirring to 273K and then 41.0 g of tosyl chloride are added in small amounts under constant temperature. After completion of the addition the mixture is left over night in the refrigerator. The reaction mixture is mixed with a water/chlorhidric acid/ice slurry, the phases are separated, washed with water and dried. The obtained solution of methane-benzene-sulfonate diester is used in the following step 3. Alkylation: Stirring into the diester solution in chloroform dissolves two equivalents of the foregoing monoazo. The temperature is raised to 333K and maintained at 333K during the following 20 hours. Crystals separated in the slurry are filtrated. The product is washed with 50 ml of chloroform and dried in vacuum to obtain 80 g of a dark solid product, which is recrystallized twice from methanol.

|  |  |  |  | Residue of compound |
|---|---|---|---|---|
| 7.966 | d | 7.3 | 3.95 | phenylen |
| 7.718 | d | 8 | 4.04 | tosylate |
| 7.564 | s |  | 3.82 | imidazol |
| 7.226 | d | 8 | 4.05 | tosylate |
| 6.927 | d | 7.8 | 3.96 | phenylen |
| 4.050 | s |  | 12.06 | dimethyl |
| 3.90 | m |  | 4.1 | methylen |
| 3.76 | m |  | 4. | methylen |
| 3.595 | t |  | 3.982 | methylen |
| 3.31 | s |  | 12 | methyl |
| 2.925 | t |  | 4.00 | methylen |
| 2.32 | s |  |  | methyl |

EXAMPLE 15

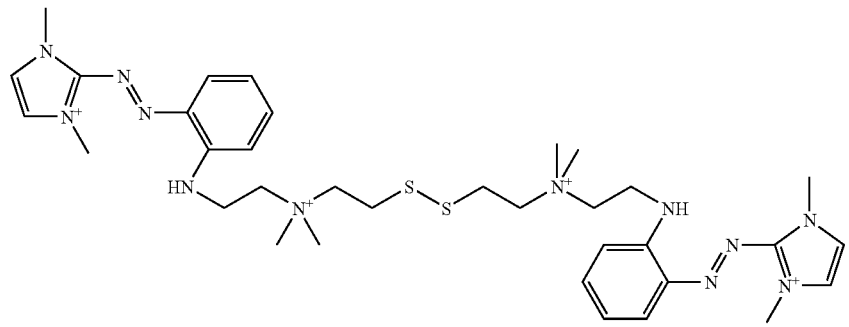

(115)

The compound of formula (102a) (prepared in example 2) is reacted with N,N-dimethyl-ethyl-lenediamine according to the procedure as described in Example A14. The same alkylating agent is used to give the compound of formula (115).

EXAMPLE A 16

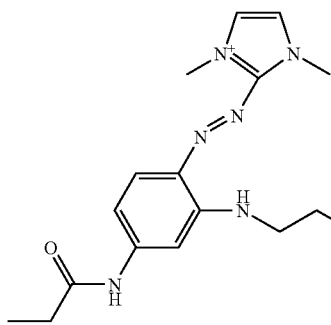
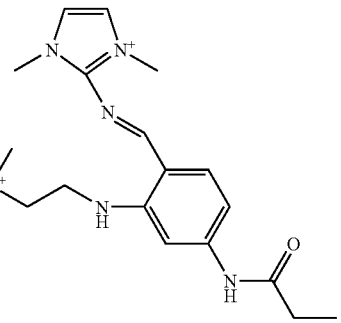

(116)

The compound of formula (104a) (prepared in example A 4) is reacted with N,N-dimethyl-ethylendiamine according to the method as described in Example A14.

The same alkylating agent is used and the compound of formula (116) is obtained.

EXAMPLE B/APPLICATION EXAMPLES

The washing fastness of the dyed hair is analyzed by the Grey scale according to Industrial organic pigments by Herbst&Hunger, 2nd ed. engl. S. 61) Nr 10: DIN 54 001-8-1982, "Herstellung und Bewertung der Aendemung der Farbe", ISO 105-A02-1993.

In the following application examples compositions with definitions the below given are used:

Solution (1) (permanent lotion, pH 8.2): Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Parfum Solution (2) (permanent fixation. DH 3.9): Based on: Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, Coco-Betaine, Acetaminophen, Phosphoric Acid, Sodium Chloride, Parfum Solution (3) (dyeing solution): 0.1% of the dye is dissolved in a 10% solution of a non-ionic surfactant (Plantacare 200UP, Henkel) adjusted to pH 9.5 using citric acid or monoethanol-amine.

Solution (4) (permanent lotion. DH 8.7): Aqua, Thioglycolic Add, Ammonium Bicarbonate, Ammonium Hydroxide, PEG-60 Hydrogenated Castor Oil, Sericin, Polyquaternium 22, Lauryidimmonium Hydroxypropyl Hydrolyzed Keratin, Hydroxyethyl Cetyldimonium Phosphate, Sodium Cocoamphopropionate, Parfum/Fragrance, Styrene/PVP Copolymer, Pantasodium Pentetate, Ascorbic Acid, Benzyl Salicilate, Hydroxyisohexyl 3-Cyclohexene Carboxaldehyde, Hexyl Cinnamal, Butylphenyl Methylprpional, Linalool.

Solution (5) (permanent fixation, pH 2.9): Based on: Aqua, Hydrogen Peroxide, Hydroxycetyl Hydroxyethyl Dimonium Chloride, Tetrasodium Etidronate, PEG-40 hydrogenated Castor Oil, Salicylic Acid, Tetrasodium EDTA, Styrene/PVP Copolymer, Sericin, Parfum/Fragrance, Phosphoric Acid.

Placebo colouring material: Obtained by adding 11 ml ammonia solution (25% b.w.) at 343K to a composition consisting of ammonium chloride 0.5% b.w., tetrasodium EDTA, 0.2% b.w., silica 0.1% b.w., water, add 100% b.w.

Then, the obtained mixture is added to a composition consisting of cetearyl alcohol, 11% b.w., oleth-5, 5% b.w., oleic acid, 2.5% b.w., stearamide MEA, 2.5% b.w., cocoamide MEA, 2.5% b.w., propylene glycol 1.0% b.w.

Coloration composition of a placebo: The coloration composition of a placebo is obtained by adding 11 ml ammonia solution (25% b.w.) at 343K to a composition consisting of ammonium chloride 0.5% b.w., tetrasodium EDTA, 0.2% b.w., silica 0.1% b.w., water, add 100% b.w. and 0.2% b.w. of a dyestuff. Then, the obtained mixture is added to a composition consisting of cetearyl alcohol, 11% b.w., oleth-5, 5% b.w., oleic acid, 2.5% b.w., stearamide MEA, 2.5% b.w., cocoamide MEA, 2.5% b.w., propylene glycol 1.0% b.w.

EXAMPLE B1

A tress of human hair, bleached white, is shampooed. Then, the towel dried hair tress is put on the glass plate. Solution (1) is applied to the wet hair tress. After 10 min the hair tress is rinsed under tap water and pressed out with a paper towel. Afterwards the tress is treated with a solution 3 containing the dye of formula (101) (Example A1) for 20 min and then rinsed with water. Then solution (2) is applied to the towel dried hair tress. After 10 minutes the hair tress is rinsed under tap water again and dried.

The tress is very intensive red with a very good wash fastness.

For comparison another tress of human hair, bleached white, is only treated with solution (3) containing the dye of formula (101) for 20 min and then rinsed with water and dried. The tress shows a less intensive red and the wash fastness is much worse.

EXAMPLE B2

A tress of blonde undamaged human hair is shampooed. Then the towel dried hair tress is put on the glass plate. The solution (1) (permanent solution) is applied to the wet hair tress. After 10 min the hair tress is rinsed under tap water and pressed out with a paper towel. Afterwards the tress is treated with a solution 3 containing the dye from Example A2 for 20 min and then rinsed with water. Then solution (2) (permanent fixation) is applied to the towel dried hair tress. After 10 min.

the hair tress is rinsed under tap water again and dried. The tress is very intensive violet with a very good wash fastness.

For comparison another tress of blonde undamaged human hair is only treated with solution 3 containing the dye for 20 min and then rinsed with water and dried. The tress is less intensive violet and the wash fastness is much worse.

EXAMPLE B3

0.1%, b.w. colouring material solution consisting of compound of formula (101) in plantaren solution (pH=9.5) is applied on the dry hair (two blond, two middle blond and two damaged hair strands) and allowed to stand for 20 min. at room temperature. Then, the strands are rinsed under tap water and dried 12 hours.

| Washing fastness: 10 × washed with shampoo/Results | | |
| --- | --- | --- |
| Strand | Colour | Washing fastness |
| blond | red | 2-3 |
| middle blond | red | 3 |
| damaged | red | 3 |

EXAMPLE B4

0.1%, b.w. colouring material solution consisting of compound of formula (101) in plantaren solution (pH=9.5) is applied on shampooed hair (two blond, two middle blond and two damaged hair strands). Then the towel dry strands are put on a glass plate and treated with solution (1) (permanent lotion) and allowed to stand for 10 min. Then, the strands are rinsed under tap water and the towel dry strands are treated with a solution (2) (permanent fixation) and allowed to stand for 10 min. Then, the strands are rinsed under tap water and dried for 12 hours at room temperature.

| Washing fastness: 10 × washed with shampoo/Results | | |
| --- | --- | --- |
| Strand | Colour | Washing fastness |
| blond | red | 5 |
| middle blond | red | 5 |
| brown | red | 5 |
| damaged | red | 5 |

EXAMPLE B5

Same application as described in example B4, but with the difference that the compound of formula (101) is rediaced by the compound of formula (102).

| Washing fastness: 10 × washed with shampoo/Results | | |
| --- | --- | --- |
| Strand | Colour | Washing fastness |
| blond | red | 5 |
| middle blond | red | 5 |
| brown | red | 5 |
| damaged | red | 5 |

EXAMPLE B6

Solution (1) (permanent lotion) is applied on shampooed hair (two blond, two middle blond and two damaged hair strands) and allowed to stand for 5 min. Then the strands are rinsed under tap water and the towel dry strands are treated with a 0.1% b.w. colouring material solution consisting of compound of formula (101) in plantaren (pH=9.5) allowed to stand for 20 min and then rinsed. Then the towel dry strands are treated with a solution (2) (permanent fixation) and allowed to stand for 10 min. Then the strands are rinsed under tap water and dried for 12 hours at room temperature.

| Washing fastness: 10 × washed with shampoo/Results | | |
| --- | --- | --- |
| Strand | Colour | Washing fastness |
| blond | red | 5 |
| middle blond | red | 5 |
| brown | red | 5 |
| damaged | red | 5 |

EXAMPLE B7

Solution (1) (permanent lotion) having a pH 8.2, which is mixed with a weight equivalent water to give a pH of 8.00 is applied on shampooed hair (two blond, two middle blond and two damaged hair strands) and allowed to stand for 10 min. Then the strands are rinsed under tap water and the towel dry strands are treated with a 0.1% b.w. colouring material solution consisting of the compound of formula (101) in plantaren (pH=9.5) and allowed to stand for 20 min and then rinsed. Then the towel dry strands are treated with solution (2) (permanent fixation) and allowed to stand for 10 min. Then the strands are rinsed under tap water and dried for 12 hours at room temperature.

| Washing fastness: 10 × washed with shampoo/Results | | |
| --- | --- | --- |
| Strand | Colour | Washing fastness |
| blond | red | 5 |
| middle blond | red | 5 |
| Brown | red | 5 |
| damaged | red | 4-5 |

EXAMPLE B8

Same application method as described in Example B7, but with the difference that the permanent wave solution allowed to stand for 5 min. instead of 10 min.

| Washing fastness: 10 × washed with shampoo/Results | | |
| --- | --- | --- |
| Strand | Colour | Washing fastness |
| blond | red | 4-5 |
| middle blond | red | 5 |
| brown | red | 5 |
| damaged | red | 4-5 |

EXAMPLE B9

Solution (1) (permanent lotion) with a pH 8.2 which is mixed with one weight equivalent water to give a pH of 8.00 is applied on shampooed hair (two blond, two middle blond and two damaged hair strands) and allowed to stand for 1 min. Then the strands are rinsed under tap water and the towel dry strands are treated with a 0.1% b.w. colouring material solution consisting of the compound of formula (101) in plantaren (pH=9.5) allowed to stand for 10 minutes and then rinsed. Then the towel dry strands are treated with solution (2) (permanent fixation) and allowed to stand for 10 min. Then the strands are rinsed under tap water and dried for 12 hours at room temperature.

| Washing fastness: 10 × washed with shampoo/Results | | |
|---|---|---|
| Strand | Colour | Washing fastness |
| blond | red | 4 |
| middle blond | red | — |
| brown | red | — |
| damaged | red | 4 |

EXAMPLE B10

A solution 1 (permanent lotion), having a pH 82, which is mixed with two weight equivalents water to give a pH of 8.0, is applied on shampooed hair (two blond, two middle blond and two damaged hair strands) and allowed to stand for 1 minutes. Then the strands are rinsed under tap water and the towel dry strands are treated with a 0.1% b.w. colouring material solution consisting of compound of formula (101) in plantaren (pH=9.5) and allowed to stand for 20 min and then rinsed. Then the towel dry strands are treated with a solution 2 (permanent fixation) and allowed to stand for 10 min. Then, the strands are rinsed under tap water and dried for 12 hours at room temperature.

| Washing fastness: 10 × washed with shampoo/Results | | |
|---|---|---|
| Strand | Colour | Washing fastness |
| blond | red | 4 |
| middle blond | red | — |
| brown | red | — |
| damaged | red | 4 |

EXAMPLE B1

A solution 1 (permanent lotion), having a pH 8.2, which is mixed with two weight equivalents water to give a pH of 8.08 is applied on shampooed hair (two blond, two middle blond and two damaged hair strands) and allowed to stand for 1 minute. Then the strands are rinsed under tap water and the towel dry strands are treated with a 0.1% b. w. colouring material solution consisting of the compound of formula (101) in plantaren (pH=9.5), allowed to stand for 10 min. and then rinsed. Then the towel dry strands are treated with a solution 2 (permanent fixation) and allowed to stand for 10 min. Then the strands are rinsed under tap water and dried for 12 hours at room temperature.

| Washing fastness: 10 × washed with shampoo/Results | | |
|---|---|---|
| Strand | Colour | Washing fastness |
| blond | red | 4 |
| middelblond | red | — |
| brown | red | — |
| damaged | red | 3 |

EXAMPLE B12

A solution 1 (permanent lotion) having a pH 8.2 is applied on shampooed hair (two blond, two middle blond and two damaged hair strands) and allowed to stand for 10 min. Then, the strands are rinsed under tap water, and the towel dry strands are treated with a colouring material solution consisting of a. compound of formula (101) according to example A1, 0.2%, b.w. solution in plantaren, and b. a watery hydrogen peroxide solution, 6% b.w., which are mixed together in a weight ratio of 1:1, and then applied on the hair and allowed to stand for 30 min. and then, rinsed and then shampooed, and afterwards dried for 12 hours at room temperature.

| Washing fastness: 10 × washed with shampoo/Results | | |
|---|---|---|
| Strand | Colour | Washing fastness |
| blond | light red | 2-3 |
| middelblond | light red | 2-3 |
| brown | light red | 4 |
| damaged | light red | 2 |

APPLICATION EXAMPLE B13

Solution 1 (permanent lotion; pH 8.2) is applied on shampooed hair (two blond, two middle blond and two damaged hair strands) and allowed to stand for 10 min. Then the strands are rinsed under tap water and the towel dry strands treated with a colouring material solution consisting of a. compound of formula (101) according to example A1, 0.2%, b.w. solution in plantaren, and b. placebo colouring material, which are mixed together in a weight ratio of 1:1, and then applied on the hair and allowed to stand for 30 min. and then rinsed.

Then the towel dry strands are treated with a solution (2) (permanent fixation), and allowed to stand for 10 min. Then the strands are rinsed under tap water and dried 12 hours at room temperature.

| Washing fastness: 10 × washed with shampoo/Results | | |
|---|---|---|
| Strand | Colour | Washing fastness |
| blond | red | 5 |
| middelblond | red | 5 |
| brown | red | 5 |
| damaged | red | 5 |

APPLICATION EXAMPLE B14

Solution (1) (permanent lotion; pH 8.2) is applied on shampooed hair (two blond, two middle blond and two damaged hair strands) and allowed to stand for 10 min. Then the strands are rinsed under tap water and the towel dry strands are treated with a 0.1%, b.w. colouring material solution consisting of the compound of formula (101) insolution (2) (permanent fixation) and allowed to stand for 20 min. Then the strands are rinsed under tap water and dried 12 hours at room temperature.

| Washing fastness: 10 × washed with shampoo/Results ||| 
|---|---|---|
| Strand | Colour | Washing fastness |
| blond | red | 5 |
| middelblond | red | 4-5 |
| brown | red | 4-5 |
| damaged | red | 3 |

APPLICATION EXAMPLE B15

A composition consisting of
a. a solution 1 (permanent lotion), having a pH 8.2, and
b. a 0.2%, b.w. solution of compound of formula (101) in plantaren, which are mixed together in a weight ratio of 1:1 is applied on shampooed hair (two blond, two middle blond and two damaged hair strands) and allowed to stand for 10 min. Then, the strands are rinsed under tap water. The towel dry strands are treated with a solution 2 (permanent fixation), and allowed to stand for 10 min. Then the strands are rinsed under tap water and dried 12 hours at room temperature.

| Washing fastness: 10 × washed with shampoo/Results ||| 
|---|---|---|
| Strand | Colour | Washing fastness |
| blond | red | 4-5 |
| middelblond | red | 5 |
| brown | red | 5 |
| damaged | red | 4-5 |

EXAMPLE B16

A composition consisting of
a. solution (1) (permanent lotion), having a pH 8.2, and
b. 0.1% b.w. solution of the compound of formula (101) in plantaren, which are mixed together in a weight ratio of 1:1, is applied on shampooed hair (two blond, two middle blond and two damaged hair strands) and allowed to stand for 20 min. Then, the strands are rinsed under tap water. The towel dry strands are treated with a solution (2) (permanent fixation), and allowed to stand for 10 min. Then the strands are rinsed under tap water and dried 12 hours at room temperature.

| Washing fastness: 10 × washed with shampoo/Results ||| 
|---|---|---|
| Strand | Colour | Washing fastness |
| blond | red | 4 |
| middelblond | red | 5 |
| brown | red | 5 |
| damaged | red | 3 |

EXAMPLE B17

A solution 1 (permanent lotion; pH 8.2) is applied on shampooed hair (two blond, two middle blond and two damaged hair strands) and allowed to stand for 20 min. Then the strands are rinsed under tap water and the towel dry strands are treated with a 0.1%, b.w. colouring material solution of compound of formula (101) in solution (2) (permanent fixation) and allowed to stand for 20 min. Then the strands are rinsed under tap water. The towel dry strands are treated with a composition consisting of a. a placebo colouring material and b. a aqueous hydrogen peroxide solution, 12% b.w., and having a weight ratio of the placebo to the hydrogen peroxide solution of 1:1. Then the strands are allowed to stand for 30 min. The strands are rinsed under tap water, shampooed and dried 12 hours at room temperature.

| Washing fastness: 10 × washed with shampoo/Results ||| 
|---|---|---|
| Strand | Colour | Washing fastness |
| blond | red | 5 |
| middelblond | red | 5 |
| brown | red | 5 |
| damaged | red | 4-5 |

EXAMPLE B18

Solution (1) (permanent lotion; pH 8.2) is applied on shampooed hair (two blond, two middle blond and two damaged hair strands) and allowed to stand for 10 min. Then the strands are rinsed under tap water and the towel dry strands are treated with a 0.1% b.w. colouring material solution of compound of formula (101) in solution (2) (permanent fixation) and allowed to stand for 20 min. Then the strands are rinsed under tap water. The towel dry strands are treated with a fixation composition consisting of a) ammonia and b) an aqueous hydrogen peroxide solution having a pH of 9.8. Then the strands are allowed to stand for 10 min. The strands are rinsed under tap water, shampooed and dried 12 hours at room temperature.

| Washing fastness: 10 × washed with shampoo/Results ||| 
|---|---|---|
| Strand | Colour | Washing fastness |
| blond | red | 5 |
| middelblond | red | 5 |
| brown | red | 5 |
| damaged | red | 4-5 |

EXAMPLE B19

A composition consisting of
a. a solution 1 (permanent lotion), having a pH 8.2, and
b. a 0.1%, b.w. solution of compound of formula (101) in plantaren which are mixed together in a weight ratio of 1:99 of component a) to b), are applied on shampooed hair (two blond, two middle blond and two damaged hair strands) and allowed to stand for 20 min. Then the strands are rinsed under tap water. The towel dry strands are treated with a fixation composition consisting of a) ammonia and b) an aqueous hydrogen peroxide solution of pH of 9.8. Then the strands are allowed to stand for 10 min. The strands are rinsed under tap water shampooed and dried 12 hours at room temperature.

| Washing fastness: 10 × washed with shampoo/Results | | |
| --- | --- | --- |
| Strand | Colour | Washing fastness |
| blond | red | 4 |
| middelblond | red | 4-5 |
| brown | red | 5 |
| damaged | red | 3-4 |

EXAMPLE B20

A colouring material solution consisting of
a. 25 ml of a 0.1% b.w. solution of compound of formula (101), and
b. 25 ml of a 0.1% b.w. solution of compound of formula (106)

is applied on dry hair (two blond, two middle blond and two damaged hair strands) and allowed to stand for 30 min.

| Washing fastness: 10 × washed with shampoo/Results | |
| --- | --- |
| Strand | Colour |
| blond | orange |
| middelblond | orange |
| brown | orange |
| damaged | orange |

EXAMPLE B21

A solution 1 (permanent lotion; pH 8.2) is applied on shampooed hair (two blond, two middle blond and two damaged hair strands) and allowed to stand for 10 min. Then the strands are rinsed under tap water, and the towel dry strands are treated with a colouring material solution consisting of
a. 25 ml of a 0.1% b.w. solution of compound of formula (101) according to example A1 in plantaren, and
b. 25 ml of a 0.1% b.w. solution of compound of formula (106) according to example A6 in plantaren solution, allowed to stand for 20 min and then rinsed.
The towel dry strands are treated with a solution (2) (permanent fixation) and allowed to stand for 10 min. The strands are rinsed under tap water and dried 12 hours at room temperature.

| Washing fastness: 10 × washed with shampoo/Results | | |
| --- | --- | --- |
| Strand | Colour | Washing fastness |
| blond | orange | 5 |
| middelblond | orange | 5 |
| brown | orange | 5 |
| damaged | orange | 5 |

EXAMPLE B22

A composition consisting of
a. Solution 4 (permanent lotion) having a pH 8.7, is mixed with one equivalent water to access pH 8.6, and
b. 0.2%, b.w. solution of the compound of formula (101) in plantaren, which are mixed together in a weight ratio of 1:1, are applied on shampooed hair (two blond, two middle blond and two damaged hair strands) and allowed to stand for 5 min. The strands are rinsed under tap water. The towel dry strands are treated with a solution (5) (permanent fixation) and allowed to stand for 10 min. The strands are rinsed under tap water and dried 12 hours at room temperature.

| Washing fastness: 10 × washed with shampoo/Results | | |
| --- | --- | --- |
| Strand | Colour | Washing fastness |
| blond | red | 5 |
| middelblond | red | 5 |
| brown | red | 5 |
| damaged | red | 5 |

EXAMPLE B23

A solution (1) (permanent lotion; pH 8.2) is applied on shampooed hair (two blond, two middle blond and two damaged hair strands) and allowed to stand for 10 min. The strands are rinsed under tap water and the towel dry strands treated with a colouring material solution consisting of
a. 0.2% b.w. solution of compound of formula (101) according to example A1, in plantaren, and
b. placebo colouring material, which are mixed together in a weight ratio of 1:1, and then applied on the hair and allowed to stand for 20 min and then rinsed.
The towel dry strands are treated with a solution 2 (permanent fixation) and allowed to stand for 10 min. The strands are rinsed under tap water and dried 12 hours at room temperature.

| Washing fastness: 10 × washed with shampoo/Results | | |
| --- | --- | --- |
| Strand | Colour | Washing fastness |
| blond | red | 5 |
| middelblond | red | 5 |
| brown | red | 5 |
| damaged | red | 5 |

EXAMPLE B24

Solution (1) (permanent lotion; pH 8.2) is applied on shampooed hair (two blond, two middle blond and two damaged hair strands) and allowed to stand for 10 min. The strands are rinsed under tap water and the towel dry strands treated with a colouring material solution consisting of
a. 0.2% b.w. solution of compound of formula (101) according to example A1, in plantaren, and
b. placebo colouring material, which are mixed together in a weight ratio of 1:1, and then, applied on the hair and allowed to stand for 10 min and then rinsed.

Then the towel dry strands are treated with solution (2) (permanent fixation) and allowed to stand for 10 min. Then the strands are rinsed under tap water and dried 12 hours at room temperature.

| Washing fastness: 10 × washed with shampoo/Results | | |
|---|---|---|
| Strand | Colour | Washing fastness |
| blond | red | 5 |
| middelblond | red | 5 |
| brown | red | 5 |
| damaged | red | 4-5 |

EXAMPLE B25

Solution (1) (permanent lotion) is applied on shampooed hair (two blond, two middle blond and two damaged hair strands) and allowed to stand for 10 min. The strands are rinsed under tap water and the towel dry strands treated with a 0.1% b. w. colouring material solution of the compound of formula (101) in plantaren, allowed to stand for 20 min and then rinsed. The towel dry strands are treated with a solution 2 (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 5 |
| middelblond | red | 4 |
| brown | red | 5 |
| damaged | red | 4 |

EXAMPLE B26

A composition consisting of
a. a solution 1 (permanent lotion), having a pH 8.2, and
b. 0.1% b.w. solution of compound of formula (101) according to example A1 in plantaren, which are mixed together in a weight ratio of 1:9 of component a) to b), is applied on shampooed hair (two blond, two middle blond and two damaged hair strands) and allowed to stand for 20 min. Then, the strands are rinsed under tap water. The towel dry strands are treated with a solution 2 (permanent fixation), and allowed to stand for 10 min. Then, the strands are rinsed under tap water and dried 12 hours at room temperature.

| Washing fastness: 10 × washed with shampoo/Results | | |
|---|---|---|
| Strand | Colour | Washing fastness |
| blond | red | 5 |
| middle blond | red | 4-5 |
| brown | red | 5 |
| damaged | red | 4 |

EXAMPLE B27

Solution (4) (permanent lotion; pH 8.7) is applied on shampooed hair (two blond, two middle blond and two damaged hair strands) and allowed to stand for 15 min. The strands are rinsed under tap water, and the towel dry strands treated with a colouring material solution consisting of
a) 1.6 weight equivalents of a 0.1% b.w. solution of compound of formula (101) according to example A1 in plantaren solution,
b) 5 weight equivalents of a 0.1% b.w. solution of compound of formula (106) according to example A6 in plantaren solution, and
c) 1.5 weight equivalents of a 0.1% b.w. solution of compound of formula (103) according to example A3 in plantaren solution, and allowed to stand for 20 min. and then rinsed. The towel dry strands are treated with solution (5) (permanent fixation; pH 2.9) and allowed to stand for 10 min. The strands are rinsed under tap water and dried for 12 hours at room temperature.

| Washing fastness: 10 × washed with shampoo/Results | | |
|---|---|---|
| Strand | Colour | Washing fastness |
| blond | brown | 4 |
| middle blond | brown | 4-5 |
| damaged | brown | 5 |
| grey 70% | brown | 5 |
| grey 90% | brown | 4-5 |

EXAMPLE B28

A colouring material solution consisting of
a 1.6 w. eq. of a 0.1% b.w. solution of the compound of formula (101) in plantaren, and
b. 5 w. eq. of a 0.1% b.w. solution of compound of formula (106) in plantaren,
c. 1.5 w. eq. of a 0.1% b.w. solution of compound of formula (103) in plantaren solution, is applied on dry hair (two blond, two middle blond and two damaged hair strands) and allowed to stand for 20 min.

| Washing fastness: 10 × washed with shampoo/Results | | |
|---|---|---|
| Strand | Colour | Washing fastness |
| blond | brown | 2-3 |
| middle blond | brown | 2-3 |
| damaged | brown | 2 |
| grey 70% | brown | 2 |
| grey 90% | brown | 2 |

EXAMPLE B29

Hair (blond strand, damaged strand) is shampooed, rolled on curls windings and then treated with solution (4) (permanent lotion; pH 8.7) and then allowed to stand for 10 min. The hair is treated with a 0.1% b.w. solution of compound of formula (101) in plantaren and allowed to stand for 20 min at room temperature. The hair is rinsed under tap water, and the towel dry strands treated with a solution 5 (permanent fixation; pH 2.9) and allowed to stand for 5 min. Curl windings are removed and the hair is again treated with solution (5) (permanent fixation; pH 3.92) and allowed to stand for 5 min. The strands are rinsed under tap water and dried 12 hours at room temperature.

The strands are curled and red coloured.

EXAMPLE B30

Hair (blond strand, damaged strand) is shampooed and then rolled on curls windings and treated with solution (4) (permanent lotion; pH 8.7 which is diluted with 2 weight equivalents of water and then allowed to stand for 5 min. The hair is treated with 0.1% b.w. solution of compound of formula (101) in plantaren and allowed to stand for 20 min at room temperature. The hair is rinsed under tap water and the towel dry strands are treated with solution (5) (permanent fixation; pH 2.9) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4 |

EXAMPLE B31

Hair (blond strand, damaged strand) is shampooed and then rolled on curls windings and treated with solution (4) (permanent lotion; pH 8.7), which is diluted with 2 weight equivalents of water and allowed to stand for 10 min. The hair treated with 0.1% b.w. solution of the compound of formula (101) in plantaren and allowed to stand for 20 min at room temperature. The hair is rinsed under tap water and the towel dry strands are treated with solution (5) (permanent fixation; pH 2.9) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4-5 |

EXAMPLE B32

A composition consisting of a. a solution 1 (permanent lotion), having a pH 8.2, which are diluted with 4 weight equivalents of water, and B. a 0.2% b.w. solution of compound of formula (101) in plantaren which are mixed together in a weight ratio of 1:2 of component a) to b), is applied on shampooed hair (two blond, two middle blond and two damaged hair strands) and allowed to stand for 20 min. Then, the strands are rinsed under tap water. The towel dry strands are treated with a solution 2 (permanent fixation), and allowed to stand for 10 mire. Then, the strands are rinsed under tap water and dried 12 hours at room temperature.

| Washing fastness: 10 × washed with shampoo/Results | | |
|---|---|---|
| strand | Colour | Washing fastness |
| blond | red | 5 |
| middle blond | red | 5 |
| brown | red | 5 |
| damaged | red | 4-5 |

EXAMPLE B33

A composition consisting of 30 g of a 0.1% b. w. solution of the compound of formula (101) in plantaren having a pH of 6.12 is applied on shampooed hair (two blond, two middle blond and two damaged hair strands) and allowed to stand for 20 min. The strands are rinsed under tap water and dried 12 hours at room temperature.

| Washing fastness: 10 × washed with shampoo/Results | | |
|---|---|---|
| strand | Colour | Washing fastness |
| blond | red | 2-4 |
| middle blond | red | 3-4 |
| brown | red | 5 |
| damaged | red | 3 |

EXAMPLE B34

A composition comprising 49.95 g of a 0.1%, b.w. solution of the compound of formula (101) in plantaren having a pH of 6.1, and 0.05 g ammonium thioglycolate solution, and ammonia and chronic acid for adjusting the pH to 8.0, is applied on shampooed hair (two blond, two middle blond and two damaged hair strands) and allowed to stand for 20 min. The strands are rinsed under tap water. The towel dry strands are treated with solution (2) (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4-5 |
| permanent waved | curled | |

EXAMPLE B35

A composition comprising 49.75 g of a 0.1% b.w. solution (pH 6.12) of the compound of formula (101), and 0.25 g ammonium thioglycolate solution, and ammonia and citric acid for adjusting the pH to 8.0, is applied on shampooed hair (two blond, two middle blond and two damaged hair strands) and allowed to stand for 20 min. The strands are rinsed under tap water. The towel dry strands are treated with a solution 2 (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4-5 |
| permanent waved | curled | |

EXAMPLE B36

A composition comprising 49.5 g of a 0.1%, b.w. solution of compound of formula (101) (pH 6.12), and 0.55 g ammonium thioglycolate solution, and ammonia and citric acid for adjusting the pH to 8.0, is applied on shampooed hair (two blond, two middle blond and two damaged hair strands) and allowed to stand for 20 min. The strands are rinsed under tap water. The towel dry strands are treated with solution (2) (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4-5 |
| permanent waved | curled | |

EXAMPLE B37

10% b.w. of a solution of sodium sulfite in water having a pH of 8 (the pH is adjusted by ammonia and citric acid) is applied on shampooed hair (blond strand, damaged strand) and allowed to stand for 10 min. The hair is rinsed and treated then with 0.1% b.w. of a solution (pH 9.5) of the compound of formula (101) and allowed to stand for 20 min at room temperature. The hair is rinsed under tap water and the towel dry strands are treated with solution (5) (permanent fixation) having a pH 2.9 and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 4-5 |

EXAMPLE B38

A composition comprising 49.95 g of a 0.1% b.w. solution of the compound of formula (101) in plantaren (pH 6.12), and 0.05 g of a 0.1% b.w. solution of sodium sulfite in water having a pH of 8 (the pH is adjusted by ammonia and citric acid), is applied on shampooed hair (two blond, two middle blond and two damaged hair strands) and allowed to stand for 20 min. The hair is rinsed under tap water and the towel dry strands are treated with solution (5) (permanent fixation) having a pH 2.9 and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4 |
| middle blond | red | 5 |
| brown | red | 4-5 |
| damaged | red | 4 |

EXAMPLE B39

A composition comprising 49 g of a 0.1% b.w. solution of the compound of formula (101) in plantaren (pH 6.12), and 1 g of a 2% b.w. solution of sodium sulfite in water having a pH of 8 (the pH is adjusted by ammonia and citric acid), is applied on shampooed hair (two blond, two middle blond and two damaged hair strands) and allowed to stand for 20 min. The hair is rinsed under tap water and the towel dry strands are treated with a solution 2 (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |

| Washing fastness: 10 × washed with shampoo/Results | | |
|---|---|---|
| Strand | Colour | Washing fastness |
| brown | red | 4-5 |
| damaged | red | 4 |
| permanent waved | red and curled | |

EXAMPLE B40

2% b.w. of a solution of sodium sulfite in water having a pH of 8 (the pH is adjusted by ammonia and citric acid) is applied on shampooed hair (blond strand, damaged strand) and then allowed to stand for 10 min. The hair is rinsed and treated then with 0.1% b.w. of a solution of the compound of formula (101) (pH 9.5) and allowed to stand for 20 min at room temperature. The hair is rinsed under tap water and the towel dry strands treated with solution (2) (permanent fixation) having a pH 3.92 and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 4-5 |
| brown | red | 5 |
| damaged | red | 4 |

EXAMPLE B41

2% b.w. of a solution of ammonium thioglycolate in water (pH 8; adjusted with ammonia and citric acid) is applied on shampooed hair (blond strand, damaged strand) and then allowed to stand for 10 min. The hair is rinsed and treated with 0.1% b.w. of a solution of the compound of formula (101) according in plantaren (pH 9.5) and allowed to stand for 20 min at room temperature. The hair is rinsed under tap water and the towel dry strands are treated with solution (2) (permanent fixation) and allowed to stand for 10 min. The strands are rinsed under tap water and dried 12 hours at room temperature.

| Washing fastness: 10 × washed with shampoo/Results | | |
|---|---|---|
| Strand | Colour | Washing fastness |
| blond | red | 4-5 |
| middle blond | red | 5 |
| brown | red | 5 |
| damaged | red | 3-4 |

EXAMPLE B42

2% b.w. of a solution of ammonium thiolactate in water (pH of 8; adjusted by ammonia and citric acid) is applied on shampooed hair (blond strand, damaged strand) and then allowed to stand for 10 min. The hair is rinsed and treated with 0.1% b.w. of a solution of the compound of formula (101) in plantaren (pH 9.5) and allowed to stand for 20 min at room temperature. The hair is rinsed under tap water and the towel dry strands treated with solution (2) (permanent fixation) and allowed to stand for 10 min. Then the strands are rinsed under tap water and dried 12 hours at room temperature.

| Washing fastness: 10× washed with shampoo/Results | | |
|---|---|---|
| Strand | Colour | Washing fastness |
| blond | red | 4-5 |
| middelblond | red | 4-55 |
| brown | red | 5 |
| damaged | red | 3-4 |

EXAMPLE B43

A composition comprising 49.95 g of a 0.1% b.w. solution of the compound of formula (101) in plantaren (pH 6.12), and 0.05 g of a 0.1% b.w. solution of ammonium thioglycolate in water having a pH of 6.1 (the pH is adjusted by ammonia and citric acid), is applied on shampooed hair (two blond, two middle blond and two damaged hair strands) and allowed to stand for 20 min. Then the strands are rinsed under tap water and dried 12 hours at room temperature.

| Washing fastness: 10× washed with shampoo/Results | | |
|---|---|---|
| Strand | Colour | Washing fastness |
| blond | red | 3-4 |
| middelblond | red | 3-4 |
| brown | red | 5 |
| damaged | red | 3-4 |

EXAMPLE B44

A composition comprising 49.95 g of a 0.1% b.w. solution of the compound of formula (101) (pH 6.12), and 0.05 g of a 0.1% b.w. solution of ammonium thioglycolate in water having a (pH of 8.0; adjusted by ammonia and citric acid), is applied on shampooed hair (two blond, two middle blond and two damaged hair strands) and allowed to stand for 20 min. Then the strands are rinsed under tap water and dried for 12 hours at room temperature.

| Washing fastness: 10× washed with shampoo/Results | | |
|---|---|---|
| Strand | Colour | Washing fastness |
| blond | red | 3-4 |
| middelblond | red | 4 |
| brown | red | 5 |
| damaged | red | 3-4 |

EXAMPLE B45

A composition comprising 49.95 g of a 0.1% b.w. solution of compound of formula (101) in plantaren (pH 6.12), and 0.05 g of a 0.1% b.w. solution of ammonium thioglycolate in water (pH 8.0; adjusted by ammonia and citric acid), is applied on shampooed hair (two blond, two middle blond and two damaged hair strands) and allowed to stand for 20 min. Then the hair is rinsed under tap water and the towel dry strands treated with a composition comprising component a) and b) in a weight ratio of 1:1, wherein a) is hydrogen peroxide, 6% b.w. solution in water, and b) is a coloration composition of a placebo and then are allowed to stand for 30 min. Then the strands are rinsed under tap water and dried 12 hours at room temperature.

| Washing fastness: 10× washed with shampoo/Results | | |
|---|---|---|
| Strand | Colour | Washing fastness |
| blond | red | 3-4 |
| middelblond | red | 4 |
| brown | red | 5 |
| damaged | red | 4 |

EXAMPLE B46

A solution of 0.1% b.w. of the compound of formula (101) in plantaren (pH 8; pH is adjusted with ethanol amin), is applied on shampooed hair (two blond, two middle blond and two damaged hair strands) and allowed to stand for 20 min. Then the hair is rinsed under tap water and dried 12 hours at room temperature.

| Washing fastness: 10× washed with shampoo/Results | | |
|---|---|---|
| Strand | Colour | Washing fastness |
| blond | red | 4 |
| middelblond | red | 4-5 |
| brown | red | 5 |
| damaged | red | 3 |

EXAMPLE B47

A solution of 0.1% b.w. of the compound of formula (101) (pH 8; adjusted with ethanolamine) is applied on shampooed hair (two blond, two middle blond and two damaged hair strands) and allowed to stand for 20 min. The hair is rinsed under tap water and the towel dry strands treated with a composition comprising component a) and b) in a weight ratio of 1:1, wherein a) is hydrogen peroxide, 6% b.w. solution in water, and b) is a coloration composition of a placebo and are allowed to stand for 30 min. The strands are rinsed under tap water and dried for 12 hours at room temperature.

| Washing fastness: 10× washed with shampoo/Results | | |
|---|---|---|
| Strand | Colour | Washing fastness |
| blond | red | 3 |
| middelblond | red | 3 |
| brown | red | 5 |
| damaged | red | 2-3 |

EXAMPLE B48

A composition comprising 49.91 g of a 0.1% b.w. solution of the compound of formula (101) in plantaren (pH 6.12), and 0.09 g of a 0.1% b.w. solution of ammonium thiolactate in water (pH of 8.0; adjusted with ammonia and citric acid), is applied on shampooed hair (two blond, two middle blond and two damaged hair strands) and allowed to stand for 20 min. Then the hair is rinsed under tap water and the towel dry strands treated with solution (2) (permanent fixation) and allowed to stand for 10 min. Then the strands are rinsed under tap water and dried for 12 hours at room temperature.

| Washing fastness: 10× washed with shampoo/Results | | |
|---|---|---|
| Strand | Colour | Washing fastness |
| blond | red | 4-5 |
| middelblond | red | 4-5 |
| brown | red | 5 |
| damaged | red | 4 |

EXAMPLE B49

A solution of 0.1% b.w. of the compound of formula (101) in plantaren (pH of 5.5; adjusted with ethanolamine) is applied on shampooed hair (two blond, two middle blond and two damaged hair strands) and allowed to stand for 20 min. Then the hair is rinsed under tap water and the towel dry strands are treated with a composition comprising component a) and b) in a weight ratio of 1:1, wherein a) is hydrogen peroxide, 6% b.w. solution in water, and b) is a coloration composition of a placebo and then allowed to stand for 30 min. The strands are rinsed under tap water and dried for 12 hours at room temperature.

| Washing fastness: 10× washed with shampoo/Results | | |
|---|---|---|
| Strand | Colour | Washing fastness |
| blond | red | 3 |
| middelblond | red | 3 |
| brown | red | 5 |
| damaged | red | 2-3 |

EXAMPLE B50

A composition comprising 49.57 g of a 0.1% b.w. solution of the compound of formula (101), and 0.43 g of a 0.1% b.w. solution of ammoniumthiolactate in water (pH 8.0; adjusted with ammonia and citric acid), is applied on shampooed hair (two blond, two middle blond and two damaged hair strands) and allowed to stand for 20 min. Then the hair is rinsed under tap water and the towel dry strands are treated with solution (2) (permanent fixation) and allowed to stand for 10 min. Then the strands are rinsed under tap water and dried for 12 hours at room temperature.

Washing fastness: 10× washed with shampoo/Results

| Strand | Colour | Washing fastness |
|---|---|---|
| blond | red | 4-5 |
| middelblond | red | 5 |
| brown | red | 5 |
| damaged | red | 4 |

APPLICATION EXAMPLE B51

A composition comprising 49.15 g of a 0.1% b.w. solution of the compound of formula (101) in plantaren (pH 6.12), and 0.85 g of a 0.1% b.w. solution of ammoniumthiolactate in water (pH 8.0; adjusted with ammonia and citric acid), is applied on shampooed hair (two blond, two middle blond and two damaged hair strands) and allowed to stand for 20 min. The hair is rinsed under tap water and the towel dry strands treated with a solution (2) (permanent fixation) and allowed to stand for 10 min. The strands are rinsed under tap water and dried 12 hours at room temperature.

Washing fastness: 10× washed with shampoo/Results

| Strand | Colour | Washing fastness |
|---|---|---|
| blond | red | 5 |
| middelblond | red | 5 |
| brown | red | 5 |
| damaged | red | 4-5 |

EXAMPLE B52

0.1% b.w. of a solution of ascobinic acid in water (pH 8; adjusted by ammonia and citric acid) is applied on shampooed hair (blond strand, damaged strand) and then allowed to stand for 10 min. Then, the hair is rinsed and treated then with 0.1% b.w. of a solution of compound of formula (101) according to example A1 in plantaren (with pH 6.1), and allowed to stand for 20 min at room temperature. Then, the hair is rinsed under tap water, and the towel dry strands are treated with a solution 2 (permanent fixation) and allowed to stand for 10 min. Then, the strands are rinsed under tap water and dried 12 hours at room temperature.

Washing fastness: 10× washed with shampoo/Results

| Strand | Colour | Washing fastness |
|---|---|---|
| blond | red | 2-3 |
| middelblond | red | 4 |
| brown | red | 5 |
| damaged | red | 2-3 |

EXAMPLE B53

2% b.w. of a solution of hydrochinon in water (pH 8; adjusted by ammonia and citric acid) is applied on shampooed hair (blond strand, damaged strand) and then allowed to stand for 10 min. The hair is rinsed and treated with 0.1% b.w. of a solution of the compound of formula (101) in plantaren solution (with pH 6.1) and allowed to stand for 20 min at room temperature. The hair is rinsed under tap water and the towel dry strands treated with a fixating solution (Goldwell) having a pH 3.92 and allowed to stand for 10 min. Then the strands are rinsed under tap water and dried 12 hours at room temperature.

Washing fastness: 10× washed with shampoo/Results

| Strand | Colour | Washing fastness |
|---|---|---|
| blond | red | 2-3 |
| middelblond | red | 4 |
| brown | red | 5 |
| damaged | red | 2-3 |

EXAMPLE B54

Test 1: A solution 1 (permanent lotion; pH 8.2) is applied on shampooed hair (two blond, two middle blond and two damaged hair strands) and allowed to stand for 10 min. Then the strands are rinsed under tap water, and the towel dry strands are treated with a 0.1% b.w. coloring material solution of a compound of formula (102) according to example A2, in plantaren and allowed to stand for 20 min. and then rinsed. The towel dry strands are treated with a solution (2) (permanent fixation) and allowed to stand for 10 min. Then the strands are rinsed under tap water and dried for 12 hours at room temperature.

Test 2: Solution (1) (permanent lotion; pH 8.2) is applied on shampooed hair (two blond, two middle blond and two damaged hair strands) and allowed to stand for 10 min. The wet strands are treated with a colouring material solution consisting of a 0.1%, b.w. colouring material solution of the compound of formula (102) in plantaren and allowed to stand for 20 min. and then rinsed. The towel dry strands are treated with solution (2) (permanent fixation) and allowed to stand for 10 min. Then the strands are rinsed under tap water and dried for 12 hours at room temperature.

Test 3: A colouring material consisting of the compound of formula (102) in plantaren is applied on dry hair and then allowed to stand for 20 min., rinsed and dried for 12 hours at room temperature.

Washing fastness: 10× washed with shampoo/Results

| Strand | Colour (test 1) | Colour (test 2) | Colour (test 3) |
|---|---|---|---|
| blond | violet/ | violet/paler than in test 3 | violet |
| middelblond | violet | violet/paler than in test 3 | violet |
| damaged | violet | violet/paler than in test 3 | violet |

-continued

Washing fastness: 10× washed with shampoo/Results

| Strand | Washing fastness (test 1) | Washing fastness (test 2) | Washing fastness (test 3) |
|---|---|---|---|
| blond | 5 | 5 | 3 |
| middelblond | 5 | 5 | 2 |
| damaged | 5 | 5 | 2-3 |

EXAMPLE B55

A solution I (pH 8.2; permanent lotion) is applied on shampooed hair (two blond, two middle blond and two damaged hair strands) and allowed to stand for 10 min. Then the strands are rinsed under tap water and the towel dry strands are treated with a colouring material solution consisting of a compound of formula (102) according to example A2, in plantaren and allowed to stand for 20 min and then rinsed. Then, the towel dry strands are treated with a solution 2 (permanent fixation), and allowed to stand for 10 min. Then, the strands are rinsed under tap water and dried 12 hours at room temperature.

Washing fastness: 10× washed with shampoo/Results

| Strand | Colour | Washing fastness |
|---|---|---|
| blond | violet | 5 |
| middelblond | violet | 5 |
| brown | violet | |
| damaged | violet | 5 |

EXAMPLE 55B

Application Example 55 is repeated with the difference that instead of a compound of formula (102) according to example A2, a compound of formula (103) according to example A3 is used.

Washing fastness: 10× washed with shampoo/Results

| Strand | Colour | Washing fastness/Example 55B |
|---|---|---|
| blond | blue | 5 |
| middelblond | blue | 5 |
| brown | blue | |
| damaged | blue | 5 |

EXAMPLE 55C

Application Example 56 is repeated with the difference that instead of a compound of formula (102) a compound of formula (106) is used.

Results

| Strand | Colour | Washing fastness/Example 55C |
|---|---|---|
| blond | yellow | 5 |
| middelblond | yellow | 5 |
| brown | yellow | |
| damaged | yellow | 5 |

EXAMPLE B56

Hair (two blond, two middle blond and two damaged hair strands) is treated with a colouring material solution consisting of a 0.1%, b.w. colouring material solution of a compound of formula (102) according to example A2, in plantaren and allowed to stand for 20 min. Then, the strands are rinsed under tap water and dried 12 hours at room temperature.

Washing fastness: 10× washed with shampoo/Results

| Strand | Colour | Washing fastness |
|---|---|---|
| blond | violet | 4 |
| middelblond | violet | 4 |
| brown | violet | |
| damaged | violet | 3-4 |

EXAMPLE 56B

Application Example 56 is repeated with the difference that instead of a compound of formula (102) a compound of formula (103) is used.

Washing fastness: 10× washed with shampoo/Results

| Strand | Colour | Washing fastness |
|---|---|---|
| blond | blue | 3 |
| middelblond | blue | 3 |
| brown | blue | |
| damaged | blue | 3 |

EXAMPLE 56C

Application Example 56 is repeated with the difference that instead of a compound of formula (102) the compound of formula (107) is used.

Washing fastness: 10× washed with shampoo/Results

| Strand | Colour | Washing fastness/ |
|---|---|---|
| blond | yellow | 5 |
| middelblond | yellow | 5 |
| brown | yellow | |
| damaged | yellow | 5 |

EXAMPLE B57

A composition comprising
49.95 g of a 0.1% b.w. solution of compound of formula (102) according to example A2 in plantaren (pH 6.12), and
0.05 g of a 0.1% b.w. solution of ammoniumthioglycolate in water having a pH of 8.0 (the pH is adjusted by ammonia and citric acid),
is applied on shampooed hair (two blond, two middle blond and two damaged hair strands) and allowed to stand for 20 min. Then, the hair is rinsed under tap water, and the towel dry strands are treated with a fixating solution (Goldwell) having a pH 3.92 and allowed to stand for 10 min. Then, the strands are rinsed under tap water and dried 12 hours at room temperature.

| Washing fastness: 10× washed with shampoo/Results | | |
|---|---|---|
| Strand | Colour | Washing fastness |
| blond | violet | 5 |
| middelblond | violet | 4-5 |
| brown | violet | — |
| damaged | violet | 3 |

EXAMPLE 57B

Application Example 57 is repeated with the difference that instead of a compound of formula (102) the compound of formula (103) is used.

| Washing fastness: 10× washed with shampoo/Results | | |
|---|---|---|
| Strand | Colour | Washing fastness |
| blond | blue | 2-3 |
| middelblond | blue | 2-3 |
| brown | blue | 4 |
| damaged | blue | 2-3 |

EXAMPLE 57C

Application Example 57 is repeated with the difference that instead of the compound of formula (102) the compound of formula (106) is used.

| Washing fastness: 10× washed with shampoo/Results | | |
|---|---|---|
| Strand | Colour | Washing fastness |
| blond | blue | 4 |
| middelblond | blue | 4 |
| brown | blue | 5 |
| damaged | blue | 4 |

EXAMPLE B58

Hair (two blond, two middle blond and two damaged hair strands) is treated with a colouring material solution consisting of a 0.1%, b.w. colouring material solution of a compound of formula (102), in plantaren and allowed to stand for 20 min. Then, the strands are rinsed under tap water and dried 12 hours at room temperature.

| Washing fastness: 10× washed with shampoo/Results | |
|---|---|
| Strand | Colour |
| blond | blue |
| middelblond | blue |
| brown | blue |
| damaged | blue |

EXAMPLE B60

A solution 4 (permanent lotion) having a pH 8.7, is applied on shampooed hair (two blond, two middle blond and two damaged hair strands) and allowed to stand for 15 min. Then, the strands are rinsed under tap water, and the towel dry strands are treated with a colouring material consisting of a 0.1%, b.w. solution of compound of formula (101) in plantaren and allowed to stand for 20 min. and then rinsed. Then, the towel dry strands are treated with a solution 5 (permanent fixation), and allowed to stand for 10 min. Then the strands are rinsed under tap water and dried 12 hours at room temperature.

| Washing fastness: 10× washed with shampoo/Results | | |
|---|---|---|
| Strand | Colour | Washing fastness |
| blond | blue | 5 |
| middelblond | blue | 5 |
| brown | blue | 5 |
| damaged | blue | 5 |

EXAMPLE B60

Hair (two blond, two middle blond and two damaged hair strands) is treated with a colouring material solution consisting of a 0.1%, b.w. solution of compound of formula (107) in plantaren, and allowed to stand for 20 min. Then, the strands are rinsed under tap water and dried 12 hours at room temperature.

| Washing fastness: 10× washed with shampoo/Results | | |
|---|---|---|
| Strand | Colour | Washing fastness |
| blond | blue | Shading: Blue-green |
| middelblond | blue | 3 |
| brown | blue | — |
| damaged | blue | 4 |

EXAMPLE B61

A solution 1 (permanent lotion), having a pH 8.2, is applied on shampooed hair (two blond, two middle blond and two damaged hair strands) and allowed to stand for 15 min. Then the strands are rinsed under tap water, and the towel dry strands are treated with a colouring material consisting of a 0.1% b.w. solution of compound of formula (101) in plantaren and allowed to stand for 20 min. and then rinsed. Then, the towel dry strands are treated with a solution 2 (permanent fixation), and allowed to stand for 10 min. Then, the strands are rinsed under tap water and dried 12 hours at room temperature.

| Washing fastness: 10× washed with shampoo/Results | | |
|---|---|---|
| Strand | Colour | Washing fastness |
| blond | blue | 4-5 |
| middelblond | blue | 4 |
| brown | blue | 5 |
| damaged | blue | 4 |

EXAMPLE B62

A composition comprising
49.95 g of a 0.1% b.w. solution of compound of formula (107) and
0.05 g of a 0.1% b.w. solution of ammonium thioglycolate in water having a pH of 8.0 (the pH is adjusted by ammonia and citric acid),
is applied on shampooed hair (two blond, two middle blond and two damaged hair strands) and allowed to stand for 20 min. Then, the hair is rinsed under tap water, and the towel dry strands are treated with a solution 2 (permanent fixation), and allowed to stand for 10 min. Then, the strands are rinsed under tap water and dried 12 hours at room temperature.

| Washing fastness: 10× washed with shampoo/Results | | |
|---|---|---|
| Strand | Colour | Washing fastness |
| blond | violet | 5 |
| middelblond | violet | 4-5 |
| brown | violet | — |
| damaged | violet | 3 |

EXAMPLE B63

309 of a 0.1% b.w. solution of compound of formula (101) in plantaren and ethanolamine (pH 10),
are applied on dry hair (two blond, two middle blond and two damaged and one blond curled hair strands) and allowed to stand for 20 min. Then, the hair is rinsed under tap water, and dried 12 hours at room temperature.

| Washing fastness: 10× washed with shampoo/Results | | |
|---|---|---|
| Strand | Colour | Washing fastness |
| blond | red | 4 |
| middelblond | red | 4-5 |
| brown | red | 5 |
| damaged | red | 3-4 |
| blond curled | red | — |

EXAMPLE B64

A composition comprising
15 g of a 0.1% b.w. solution of compound of formula (103) and
50 g of a 0.1% b.w. solution of compound of formula (106) according to example A6 in water, are applied on dry hair (two blond, two middle blond and two damaged hair strands) and allowed to stand for 20 min. Then, the hair is rinsed under tap water, and dried 12 hours at room temperature.

| Washing fastness: 10× washed with shampoo/Results | | |
|---|---|---|
| Strand | Colour | Washing fastness |
| blond | green | 4 |
| middelblond | green | 4-5 |
| brown | green | 5 |
| damaged | green | 3-4 |

EXAMPLE B65

A solution 4 (permanent lotion) having a pH 8.7, is applied on shampooed hair (two blond, two middle blond and two damaged hair strands) and allowed to stand for 15 min. Then, the strands are rinsed under tap water, and the towel dry strands are treated with a colouring material consisting of a 0.1%, b.w. solution of compound of formula (101) according to example A1, in water and allowed to stand for 20 min. and then rinsed. Then, the towel dry strands are treated with a solution 5 (permanent fixation), and allowed to stand for 10 min. Then, the strands are rinsed under tap water, and then shampooed.

Then, a solution 4 (permanent lotion) having a pH 8.7, is applied on the shampooed hair (two blond, two middle blond and two damaged hair strands) and allowed to stand for 15 min.

Then, the strands are rinsed under tap water, and the towel dry strands are treated with a colouring material comprising
15 g of a 0.1%, b.w. solution of compound of formula (103) in water, and
50 g of a 0.1%, b.w. solution of compound of formula (106), in water
and allowed to stand for 20 min. and then rinsed. Then, the towel dry strands are treated with a solution 5 (permanent fixation), and allowed to stand for 10 min. Then the strands are rinsed under tap water, and dried for 12 hours at room temperature.

| Washing fastness: 10× washed with shampoo/Results | | |
|---|---|---|
| Strand | Colour | Washing fastness |
| blond | red-brown | 5 |
| middelblond | red | 5 |
| brown | red | 5 |
| damaged | red | 5 |

The invention claimed is:

1. Method of dyeing keratin-containing fibers comprising treating the fiber with at least one sulfide dye of formula $$R_1\text{---}(Z_1)r\text{---}Y_1\text{---}S\text{---}Z_3\text{---}[Y_2\text{---}(Z_2)q\text{---}R_2]_n, \quad (1)$$

wherein
$R_1$ and $R_2$ each independently from each other are a residue of an organic dye;
$Y_1$ and $Y_2$ each independently from each other are unsubstituted or substituted, straight-chain or branched, interrupted or uninterrupted —$C_1$-$C_{10}$alkylene-; —$C_5$-$C_{10}$cycloalkylene-; 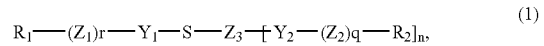 $C_5$-$C_{10}$arylene; or —$C_5$-$C_{10}$arylene-($C_1$-$C_{10}$alkylene)-;
$Z_1$ and $Z_2$ independently from each other are —C(O); —$C_2$-$C_{12}$alkenylene-; —(CH$_2$CH$_2$—O)$_{1-5}$—; —$C_1$-$C_{10}$alkylene($C_5$-$C_{10}$arylene)-; —$C_5$-$C_{10}$arylene-; —$C_5$-$C_{10}$cycloalkylene-; —C(O)O—;

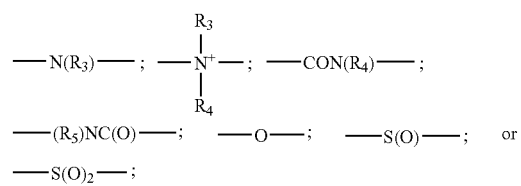

R$_3$, R$_4$ and R$_5$ are each independently from each other hydrogen; or unsubstituted or substituted, straight-chain or branched, monocyclic or polycyclic, interrupted or uninterrupted C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_5$-C$_{10}$alkyl(C$_5$-C$_1$aryl);

r, q and n independently from each other are 0 or 1, if n is 0,

Z$_3$ is hydrogen; and if n is 1,

Z$_3$ is —S—;

with the proviso that the method does not comprise treating the fiber with an enzyme of the type of a protein disulfidisomerase (EC 5.3.4.1).

2. Method according to claim 1, wherein
Y$_1$ and Y$_2$ are unsubstituted or substituted straight-chain or branched, interrupted or uninterrupted —C$_6$-C$_{10}$cycloalkylene-; or —C$_1$-C$_{10}$alkylene.

3. Method according to claim 1 or 2, wherein
n is 1.

4. Method according to claim 1 or 2, wherein
n is 0.

5. Method according to any of claims 1 to 4, wherein
R$_1$ and R$_2$ are identical.

6. Method according to any of claims 1 to 4, wherein
Z$_1$ and Z$_2$ independently from each other are

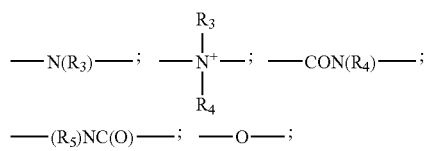

or —S—; and
R$_3$, R$_4$ or R$_5$ are defined as in claim 1.

7. Method according to any claims 1 to 6, wherein at least one sulfide dye of formula

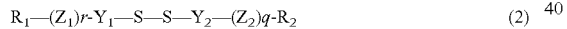     (2)

and/or at least one sulfide dye of formula

     (3)

is used, wherein
R$_1$, R$_2$, Z$_1$, Z$_2$, Y$_1$, Y$_2$, r and q are defined in claim 1.

8. Method according to any of claims 1 to 7, wherein R$_1$ and R$_2$ are selected from the group of anionic, cationic, neutral, amphoter and zwitterionic dyes.

9. Method according to any of claims 1 to 8, wherein R$_1$ and R$_2$ are selected from the group of cationic dyes.

10. Method according to any of claims 1 to 8, wherein R$_1$ and R$_2$ are selected from the group of anthraquinone, acridine dye, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, styryl, triphenylmethane, xanthene, thiazine dye and thioxanthene dyes.

11. Method according to claim 10, wherein R$_1$ and R$_2$ are selected from azo, azomethine, hydrazomethine, merocyanine, methine and styryl dyes.

12. Method according to any of claims 1 to 11, wherein R$_1$ and R$_2$ are selected from azo, azomethine and hydrazomethine dyes.

13. Method according to any of claims 1 to 12 comprising treating the keratin-containing fiber with at least one sulfide dye selected from the dyes of formula

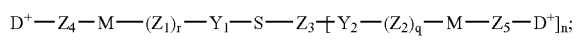     (7)

and

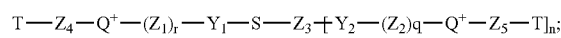     (8)

wherein
Z$_4$ and Z$_5$ independently from each other are a bivalent radical selected from —N=N—; —CR$_6$=N—; —N=CR$_7$—; —NR$_8$—N=CR$_9$—; and —R$_{10}$C=N—NR$_{11}$—; wherein R$_6$, R$_7$, R$_8$, R$_9$, R$_{10}$ and R$_{11}$ independently from each other are hydrogen; unsubstituted or substituted C$_1$-C$_{14}$alkyl; C$_2$-C$_{14}$alkenyl; C$_5$-C$_{10}$aryl; C$_1$-C$_{10}$alkyl-C$_5$-C$_{10}$aryl; or C$_5$-C$_{10}$aryl-C$_1$-C$_{10}$alkyl; and D$^+$ is a cationic radical of a substituted or unsubstituted aromatic or heterocyclic compound, wherein the cationic charge may be part of the aromatic compounds or part of the substituent;

M is a bivalent radical of an aromatic or heteroaromatic substituted or unsubstituted compound;

T is a radical of an aromatic substituted or unsubstituted compound;

Q$^+$ is a cationic biradical of a substituted or unsubstituted aromatic or heteroaromatic compound; and Z$_1$, Z$_2$, Z$_3$, Y$_1$, Y$_2$, n, r and q are defined as in claim 1.

14. Method according to claim 13, wherein D$^+$ is selected from a radical of a cationic aromatic heterocyclic compound of the formulae

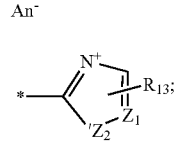     (9)

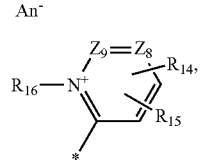     (10)

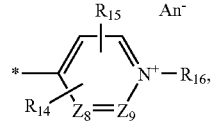     (10')

-continued

(11)
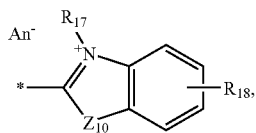

(12)
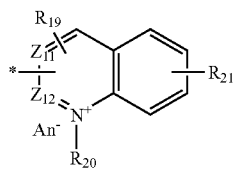

or

(13)
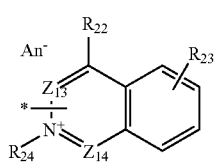

wherein
the asterix * indicates the bond to $Z_4$ and/or $Z_5$ of formula (7); and
$Q^+$ is a cationic bivalent radical of an aromatic heterocyclic compound of formulae

(14)
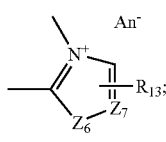

(15)
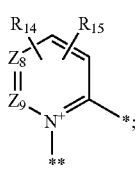

(15')
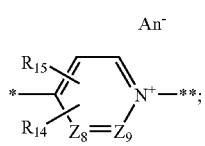

(16)
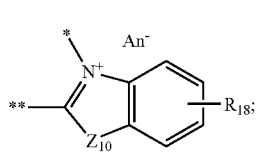

(17)
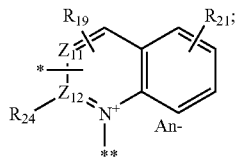

or

(18)
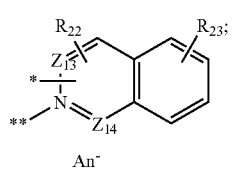

wherein
the asterix * indicates a bond to $Z_4$ and/or $Z_5$ of formula (8);
the asterix ** is a bond to $Z_1$ and/or $Z_2$ of formula (8); and
M is a bivalent radical of formulae

(19)
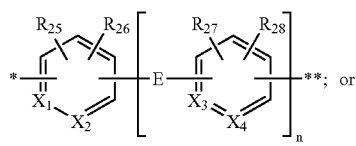

(20)
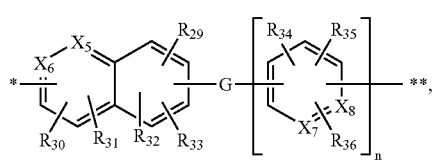

wherein
the asterix * indicates the bond to $Z_4$ or/and $Z_5$ of formula (7);
the asterix ** indicates the bond to $Z_1$ and/or $Z_2$ of formula (7); and
T is a radical of the compounds of formulae

(21)
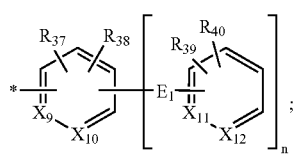

or

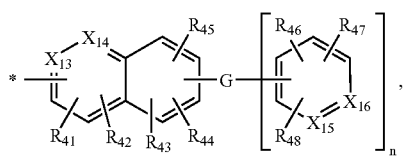
(22)

wherein
the asterix * indicates the bond to $Z_4$ and/or $Z_5$ of compound of formula (8);

$X_1, X_2, X_3, X_4, X_5, X_6, X_7, X_8, X_9, X_{10}, X_{11}, X_{12}, X_{13}, X_{14}, X_{15}$ and $X_{16}$ are independently from each other N or a radical of $CR_{49}$, Z is —O—; —S—; or a radical of $NR_{50}$, $Z_7, Z_8, Z_9, Z_{10}, Z_{11}, Z_{12}, Z_{13}$ and $Z_{14}$ are independently from each other N or a radical of $CR_{51}$;

E, $E_1$, G and $G_1$ are independently from each other —O—, —S—, —(SO$_2$)—, —$C_1$-$C_{10}$alkylene or —(NR$_{52}$)—;

$R_{13}, R_{14}, R_{15}, R_{18}, R_{19}, R_{21}, R_{22}, R_{23}, R_{25}, R_{26}, R_{27}, R_{28}, R_{29}, R_{30}, R_{31}, R_{32}, R_{33}, R_{34}, R_{35}, R_{36}, R_{37}, R_{38}, R_{39}, R_{40}, R_{41}, R_{42}, R_{43}, R_{44}, R_{45}, R_{46}, R_{47}, R_{48}, R_{49}$ and $R_{51}$ are independently from each other hydrogen; halogen; $C_1$-$C_{14}$alkyl, which is saturated or unsaturated, linear or branched, substituted or unsubstituted, or interrupted or uninterrupted with heteroatoms; a radical of phenyl, which substituted or unsubstituted; a of carboxylic acid radical; sulfonic acid radical; hydroxy; nitrile; $C_1$-$C_{16}$alkoxy, (poly)-hydroxy-$C_2$-$C_4$-alkoxy; halogen; sulfonylamino; $SR_{60}$; $NHR_{53}$; $NR_{54}R_{55}$; $OR_{61}$; $SO_2$; $COOR_{62}$; $NR_{56}COR_{58}$; or $CONR_{57}$; and $R_{12}, R_{16}, R_{17}, R_{20}, R_{24}, R_{50}, R_{52}, R_{53}, R_{54}, R_{55}, R_{56}, R_{57}, R_{58}, R_{60}, R_{61}$ and $R_{62}$ are each independently of the other hydrogen; unsubstituted or substituted $C_1$-$C_{14}$alkyl, $C_2$-$C_{14}$alkenyl, $C_5$-$C_{10}$aryl, $C_5$-$C_{10}$aryl-($C_1$-$C_{10}$alkyl), or —$C_1$-$C_{10}$alkyl($C_5$-$C_{10}$aryl); and An is an anion.

15. Method according to any of claims 1 to 14, wherein $D^+$ is a radical of a cationic aromatic substituted or unsubstituted heterocyclic compound of formulae

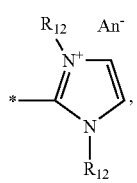
(23)

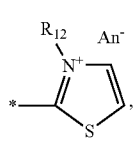
(24)

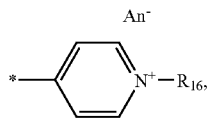
(25)

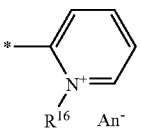
(26)

or

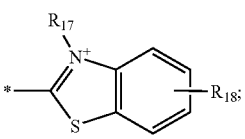
(27)

wherein
* is a bond to $Z_4$ and/or $Z_6$ of formula (7); and
$Q^+$ is a biradical of a cationic aromatic substituted or unsubstituted heterocyclic compound of formulae

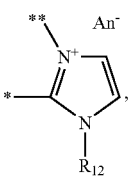
(28)

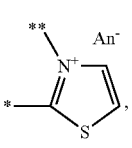
(29)

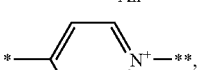
(30)

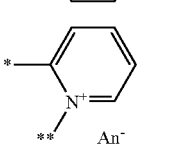
(31)

or

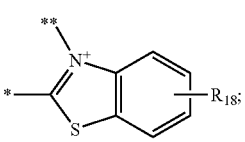
(32)

wherein
* is a bond to $Z_4$ and/or $Z_5$ of formula (8);
** is a bond to and $Z_1$ and/or $Z_2$ of formula (8); and
M is a bivalent radical of formula

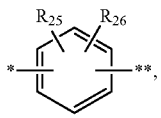

(33)

wherein
* is a bond to $Z_4$ and/or $Z_5$ of formula (7) or (8),
** is a bond to and $Z_1$ and/or $Z_2$ of formula (7) or (8); and
n is 1 or 0;
and
T is a radical of formulae

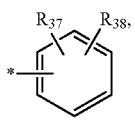

(34)

wherein
$R_{12}, R_{16}, R_{17}, R_{18}, R_{25}, R_{26}, R_{37}, R_{38}$ and An are defined as in claim 14.

16. A method according to any of claims 1 to 15 wherein the dyeing with the compounds of formula (1) is carried out in the presence of a reduction agent.

17. A method according to claim 16, wherein the reducing agent is selected from thioglycol acid or salts thereof, glycerine monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

18. A method according to one of claims 1 to 17, comprising treating the keratin-containing fiber
a) optionally with a reduction agent, and
b) at least one single sulfide dye of formula (1) as defined in claim 1, and
c) optionally with an oxidizing agent.

19. A method according to any of claims 1 to 18, comprising
a. dyeing the keratin-containing fiber with a compound of formula (1),
b. wearing the coloured hair for the desired period of time,
c. removing the colour applied in step a) from hair by contacting the hair with an aqueous based colour removal composition containing a reducing agent capable of disrupting the —S—S— bonds between the dye molecule and the hair fiber surface to cause the dye molecule to become disassociated from the hair fiber.

20. A composition comprising at least one dye of formula (1) as defined in claim 1.

21. A composition according to claim 20 in form of a shampoo, conditioner, gel or emulsion.

22. A composition according to claim 20 or 21 comprising at least one single dye of formula (1) as defined in claim 1 and a direct dye and/or a reactive dye.

23. Compounds of formula

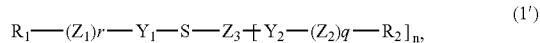

(1')

wherein
$R_1$ and $R_2$ each independently from each other are a residue of an organic dye;
$Y_1$ and $Y_2$ independently from each other are $C_1$-$C_{10}$alkylene;
$Z_1$ and $Z_2$ independently from each other are —C(O)—; —$C_2$-$C_{12}$alkenylene-; —(CH$_2$CH$_2$—O)$_{1-5}$—; $C_1$-$C_{10}$alkylene($C_5$-$C_{10}$arylene); $C_5$-$C_{10}$arylene; $C_5$-$C_{10}$cycloalkylene, —C(O)O—, —OCO—;

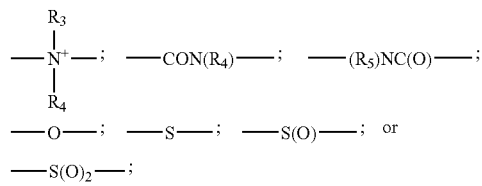

$R_3$, $R_4$, and $R_5$ are each independently from each other hydrogen; $C_1$-$C_{14}$alkyl; $C_2$-$C_{14}$alkenyl; $C_6$-$C_{10}$aryl; $C_1$-$C_5$alkyl-$C_5$-$C_{10}$aryl; or —$C_5$-$C_{10}C_5$-$C_{10}$aryl;
r, q and n independently from each other are 0; or 1,
if n is 0,
$Z_3$ is hydrogen; and
if n is 1,
$Z_3$ is —S—.

24. Compounds of formulae

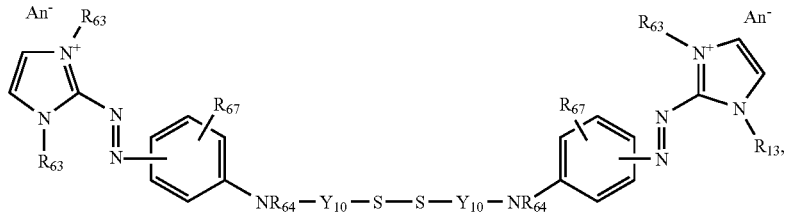

(35)

wherein
$R_{63}$ is hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl-($C_1$-$C_{10}$alkyl); $C_1$-$C_{10}$alkyl-($C_5$-$C_{10}$aryl); $C_5$-$C_{10}$aryl; and
$R_{64}$ is hydrogen; unsubstituted or substituted, straight-chain or branched, interrupted or uninterrupted $C_1$-$C_{14}$alkyl, $C_5$-$C_{10}$cycloalkyl, $C_5$-$C_{10}$aryl, or $C_5$-$C_{10}$aryl-($C_1$-$C_{10}$alkyl); $C_1$-$C_{10}$alkyl($C_5$-$C_{10}$aryl);

$R_{67}$ is hydrogen; or a radical of formula

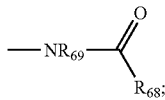
(35a)

$Y_{10}$ is unsubstituted or substituted, straight-chain or branched, monocyclic, from $C_3$-alkyl upwards, or polycyclic, from $C_5$-alkyl upwards, interrupted or uninterrupted, $C_1$-$C_{10}$alkylene; $C_5$-$C_{10}$arylene-($C_1$-$C_{10}$alkylene); $C_1$-$C_{10}$alkylene-($C_5$-$C_{10}$arylene); or —$C_5$-$C_{10}$arylene; and $R_{68}$ and $R_{69}$ are each independently of the other hydrogen, unsubstituted or substituted $C_1$-$C_{14}$alkyl, $C_2$-$C_{14}$alkenyl, —$C_5$-$C_{10}$arylen-($C_1$-$C_{10}$alkyl), —$C_1$-$C_{10}$alkylen($C_5$-$C_{10}$aryl), $C_5$-$C_{10}$aryl,

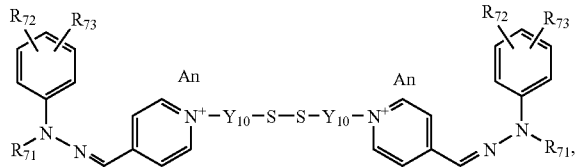
(36)

wherein $R_{71}$ is hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl; $C_1$-$C_{10}$alkyl-($C_5$-$C_{10}$aryl); $C_5$-$C_{10}$aryl-($C_1$-$C_{10}$alkyl);

$R_{72}$ and $R_{73}$ are each independently of the other hydrogen; $C_1$-$C_{14}$alkyl; $C_2$-$C_{14}$alkenyl; a radical of acarboxylic; a radical of a sulfonic acid; $C_5$-$C_{10}$aryl; hydroxy, nitril, $C_1$-$C_{16}$alkoxy, (poly)-hydroxy-$C_2$-$C_4$-alkoxy, carboxylic acid; halogen; sulfonylamino; $SR_{60}$; $NHR_{53}$; $NR_{54}R_{55}$; $OR_{61}$; $COOR_{62}$; $NR_{56}COR_{58}$; or $CONR_{57}$;

$R_{53}$, $R_{54}$, $R_{55}$, $R_{56}$, $R_{57}$, $R_{58}$, $R_{60}$, $R_{61}$, and $R_{62}$ are each independently of the other hydrogen; unsubstituted or substituted $C_1$-$C_{14}$alkyl; $C_2$-$C_{14}$alkenyl; —$C_5$-$C_{10}$arylen-($C_1$-$C_{10}$alkyl); —$C_1$-$C_{10}$alkylene($C_5$-$C_{10}$aryl); or $C_5$-$C_{10}$aryl;

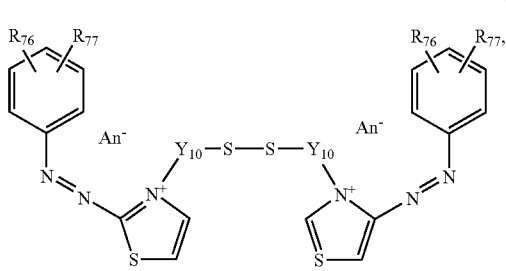
(37)

wherein $R_{76}$ and $R_{77}$ are each independently of the other hydrogen, $C_1$-$C_{14}$alkyl, which is saturated or unsaturated, linear or branched, substituted or unsubstituted, or interrupted or uninterrupted with heteroatoms; a radical of phenyl, which substituted or unsubstituted; a radical of carboxylic acid; $C_5$-$C_{10}$aryl; a radical of hydroxy, nitril, $C_1$-$C_{16}$alkoxy, (poly)-hydroxy-$C_2$-$C_4$-alkoxy, carboxylic acid, sulfonic acid; halogen, sulfonylamino, $SR_{60}$, $NHR_{53}$ or $NR_{54}R_{55}$ $OR_{61}$, $SO_2$, $COOR_{62}$, $NR_{56}COR_{58}$, $CONR_{57}$;

$R_{53}$, $R_{54}$, $R_{55}$, $R_{56}$, $R_{57}$, $R_{58}$, $R_{60}$, $R_{61}$ and $R_{62}$ are each independently of the other hydrogen, unsubstituted or substituted $C_1$-$C_{14}$alkyl, $C_2$-$C_{14}$alkenyl, —$C_5$-$C_{10}$aryl-($C_1$-$C_{10}$alkyl), —$C_1$-$C_{10}$alkyl($C_5$-$C_{10}$aryl) or $C_6$-$C_{10}$aryl;

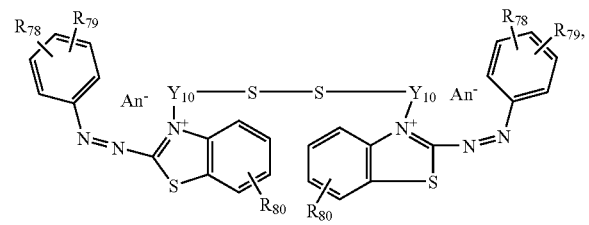
(38)

wherein $R_{79}$, $R_{78}$ and $R_{80}$ are each independently of the other hydrogen; $C_1$-$C_{14}$alkyl, which is saturated or unsaturated, linear or branched, substituted or unsubstituted, or interrupted or uninterrupted with heteroatoms; a radical of phenyl, which substituted or unsubstituted; a radical of carboyxlic acid; $C_5$-$C_{10}$aryl a radical of hydroxy, nitril, $C_1$-$C_{16}$alkoxy, (poly)-hydroxy-$C_2$-$C_4$-alkoxy; carboxylic acid; sulfonic acid; halogen; sulfonylamino; $SR_{50}$; $NHR_{53}$; $NR_{54}R_{55}$; $OR_{61}$; $SO_2$; $COOR_{62}$; $NR_{56}COR_{58}$; or $CONR_{57}$;

$R_{53}$, $R_{54}$, $R_{55}$, $R_{56}$, $R_{57}$, $R_{58}$, $R_{60}$, $R_{61}$ and $R_{62}$ are each independently of the other hydrogen; unsubstitued or substituted $C_1$-$C_{14}$alkyl; $C_2$-$C_{14}$alkenyl; $C_5$-$C_{10}$arylene-($C_1$-$C_{10}$alkyl), $C_1$-$C_{10}$alkylene($C_5$-$C_{10}$aryl), $C_5$-$C_{10}$aryl; and An is an anion.

25. A process for the preparation of compounds of formula (1) according to claim 1, which comprises reacting a compound of formula (1a) with the compound of formula (1b) according to the following reaction scheme:

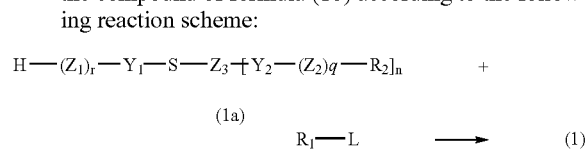

wherein

L is a leaving group; and $R_1$, $R_2$, $Y_1$, $Y_2$, $Z_2$, $Z_3$, q and r are defined as in claim 1.

26. A process for the preparation of compounds of formula (1) according to claim 1, which comprises reacting a compound of formula (1c) with the compound of formula (1d) according to the following reaction scheme:

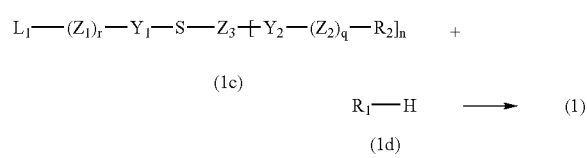

wherein $L_1$ is a leaving group; and $R_1$, $R_2$, $Z_1$, $Z_2$, $Z_3$, $Y_1$, $Y_2$, r, q and n are defined as in claim 1.

* * * * *

UNITED STATES PATENT AND TRADEMARK OFFICE
CERTIFICATE OF CORRECTION

PATENT NO. : 7,476,260 B2  Page 1 of 3
APPLICATION NO. : 11/547571
DATED : January 13, 2009
INVENTOR(S) : Victor Paul Eliu et al.

It is certified that error appears in the above-identified patent and that said Letters Patent is hereby corrected as shown below:

In column 72

Line 40, replacement of "Method", with "A method".

In column 73

Line 5, replacement of "$C_5$-$C_{10}$alkyl($C_5$-$C_1$aryl)", with "$C_5$-$C_{10}$alkyl($C_5$-$C_{10}$aryl)".

In column 73

Line 14, replacement of "Method", with "A method".

In column 73

Line 18, replacement of "Method", with "A method".

In column 73

Line 18, replacement of "claim 1 or 2", with "claim 1".

In column 73

Line 21, replacement of "Method", with "A method".

In column 73

Line 21, replacement of "claim 1 or 2", with "claim 1".

In column 73

Line 23, replacement of "Method", with "A method".

In column 73

Line 23, replacement of "any of claims 1 to 4", with "claim 1".

In column 73

Line 25, replacement of "Method", with "A method".

Signed and Sealed this

Seventeenth Day of August, 2010

David J. Kappos
*Director of the United States Patent and Trademark Office*

In column 73

Line 25, replacement of "any of claims 1 to 4", with "claim 1".

In column 73

Line 38, replacement of "Method", with "A method".

In column 73

Line 38, replacement of "any of claims 1 to 6", with "claim 1".

In column 73

Line 47, replacement of "Method", with "A method".

In column 73

Line 47, replacement of "any of claims 1 to 7", with "claim 1".

In column 73

Line 49, replacement of "amphoter", with "amphoteric".

In column 73

Line 50, replacement of "Method", with "A method".

In column 73

Line 50, replacement of "any of claims 1 to 8", with "claim 1".

In column 73

Line 52, replacement of "Method", with "A method".

In column 73

Line 52, replacement of "any of claims 1 to 8", with "claim 1".

In column 73

Line 62, replacement of "Method", with "A method".

In column 73

Line 65, replacement of "Method", with "A method".

In column 73

Line 65, replacement of "any of claims 1 to 11", with "claim 1".

In column 74

Line 1, replacement of "Method", with "A method".

In column 74

Line 1, replacement of "any of claims 1 to 12", with "claim 1".

In column 74

Line 43, replacement of "Method", with "A method".

In column 77

Line 19, replacement of "Z is", with "$Z_6$ is".

In column 77

Line 44, replacement of "Method", with "A method".

In column 77

Line 44, replacement of "any of claims 1 to 14", with "claim 1".

In column 78

Line 22, replacement of "and/or $Z_6$", with "and/or $Z_5$".

In column 79

Line 27, replacement of "any of claims 1 to 15", with "claim 1".

In column 79

Line 36, replacement of "any of claims 1 to 17", with "claim 1".

In column 79

Line 57, replacement of "any of claims 1 to 18", with "claim 18".

In column 80

Line 5, replacement of "claim 20 or 21", with "claim 20".

In column 80

Line 36, replacement of "or -$C_5C_{10}C_5$-$C_{10}$aryl", with "or -$C_5$-$C_{10}$aryl".

In column 81

Line 36, replacement of "acarboxylic", with "a carboxylic acid;".

In column 82

Line 8, replacement of "or $C_6$-$C_{10}$aryl", with "or $C_5$-$C_{10}$aryl".